United States Patent
Li et al.

(10) Patent No.: US 10,452,100 B2
(45) Date of Patent: Oct. 22, 2019

(54) METHOD AND APPARATUS FOR MANAGING BODY DEVICE

(71) Applicant: HUAWEI TECHNOLOGIES CO., LTD., Shenzhen, Guangdong (CN)

(72) Inventors: Yingtao Li, Shenzhen (CN); Xijun Xue, Beijing (CN); Yun Lei, Beijing (CN); Tao Huang, Beijing (CN)

(73) Assignee: HUAWEI TECHNOLOGIES CO., LTD., Shenzhen (CN)

( * ) Notice: Subject to any disclaimer, the term of this patent is extended or adjusted under 35 U.S.C. 154(b) by 36 days.

(21) Appl. No.: 15/606,192

(22) Filed: May 26, 2017

(65) Prior Publication Data

US 2017/0262015 A1    Sep. 14, 2017

Related U.S. Application Data

(63) Continuation of application No. PCT/CN2015/074923, filed on Mar. 24, 2015.

(30) Foreign Application Priority Data

Nov. 29, 2014    (CN) .......................... 2014 1 0712732

(51) Int. Cl.
*G06F 1/16*    (2006.01)
*H04L 29/08*    (2006.01)
(Continued)

(52) U.S. Cl.
CPC ............ *G06F 1/163* (2013.01); *A61B 5/0002* (2013.01); *A61B 5/0022* (2013.01);
(Continued)

(58) Field of Classification Search
CPC ........ G16H 40/67; G16H 50/20; G16H 40/63; G06F 19/00; G06F 1/163; G06F 19/3418;
(Continued)

(56) References Cited

U.S. PATENT DOCUMENTS 8,998,830 B2 *  4/2015  Halperin ................ A61B 5/002
                                                          600/300
2007/0066315 A1   3/2007  Kado
(Continued)

FOREIGN PATENT DOCUMENTS

CN       101642370 A      2/2010
CN       202533944 U     11/2012
(Continued)

OTHER PUBLICATIONS

Chinese Office Action dated Apr. 3, 2018, in corresponding Chinese Patent Application No. 201410712732.3, 9 pgs.
(Continued)

*Primary Examiner* — Joseph H Feild
*Assistant Examiner* — Sharmin Akhter
(74) *Attorney, Agent, or Firm* — Conley Rose, P.C.

(57) ABSTRACT

The present invention relates to the computer field, and specifically, to a method and an apparatus for managing a body device. The method includes: obtaining, by a mobile personal station, an identifier of a body device; obtaining, by the mobile personal station according to the identifier of the body device, a communication mode supported by the body device; obtaining, by the mobile personal station, a body parameter and a location parameter that are of a user that carries the body device; and setting, by the mobile personal station, the body device according to the body parameter, the location parameter, and the communication mode supported by the body device. In this way, the body device can be set quickly, which facilitates management of the body device and improves user experience.

20 Claims, 15 Drawing Sheets

(51) Int. Cl.

| | |
|---|---|
| *G16H 40/63* | (2018.01) |
| *A61B 5/00* | (2006.01) |
| *H04B 1/3888* | (2015.01) |
| *H04Q 9/02* | (2006.01) |
| *H04W 4/02* | (2018.01) |
| *A61B 5/021* | (2006.01) |
| *A61B 5/024* | (2006.01) |
| *G06F 19/00* | (2018.01) |
| *H04B 1/3827* | (2015.01) |
| *G16H 40/67* | (2018.01) |
| *G16H 50/20* | (2018.01) |
| *H04W 4/90* | (2018.01) |
| *H04W 4/70* | (2018.01) |
| *H04W 84/18* | (2009.01) |

(52) U.S. Cl.
CPC ............ *A61B 5/0024* (2013.01); *A61B 5/021* (2013.01); *A61B 5/02438* (2013.01); *A61B 5/6802* (2013.01); *A61B 5/7282* (2013.01); *A61B 5/746* (2013.01); *G06F 19/3418* (2013.01); *G16H 40/63* (2018.01); *G16H 40/67* (2018.01); *G16H 50/20* (2018.01); *H04B 1/385* (2013.01); *H04B 1/3888* (2013.01); *H04L 29/08* (2013.01); *H04Q 9/02* (2013.01); *H04W 4/02* (2013.01); *H04W 4/70* (2018.02); *H04W 4/90* (2018.02); *A61B 5/686* (2013.01); *H04B 2001/3861* (2013.01); *H04L 67/12* (2013.01); *H04W 4/025* (2013.01); *H04W 84/18* (2013.01)

(58) Field of Classification Search
CPC ........... H04W 4/70; H04W 4/90; H04W 4/02; A61B 5/0002; A61B 5/0022; A61B 5/0024; A61B 5/021; A61B 5/02438; A61B 5/6802; A61B 5/7282; A61B 5/746; H04B 1/385; H04B 1/3888; H04L 29/08; H04Q 9/02
USPC ........................................... 340/573.1–573.4
See application file for complete search history.

(56) References Cited

U.S. PATENT DOCUMENTS

| | | | |
|---|---|---|---|
| 2009/0058635 | A1 | 3/2009 | Lalonde et al. |
| 2009/0063187 | A1* | 3/2009 | Johnson .............. A61B 5/411 |
| | | | 705/2 |
| 2012/0154143 | A1* | 6/2012 | D'Ambrosio .......... A61B 5/686 |
| | | | 340/539.11 |
| 2012/0182939 | A1 | 7/2012 | Rajan et al. |
| 2014/0218184 | A1 | 8/2014 | Grant et al. |
| 2014/0267299 | A1* | 9/2014 | Couse .................. G06T 11/206 |
| | | | 345/440.2 |
| 2015/0188916 | A1 | 7/2015 | Yamada et al. |
| 2016/0119297 | A1 | 4/2016 | Sundaram et al. |
| 2017/0000385 | A1 | 1/2017 | Chen |
| 2017/0091437 | A1 | 3/2017 | Lee et al. |

FOREIGN PATENT DOCUMENTS

| | | |
|---|---|---|
| CN | 202548844 U | 11/2012 |
| CN | 103458532 A | 12/2013 |
| CN | 103584848 A | 2/2014 |
| CN | 103970208 A | 8/2014 |
| CN | 103995607 A | 8/2014 |
| CN | 104042198 A | 9/2014 |
| JP | 2007074564 A | 3/2007 |
| JP | 2008206061 A | 9/2008 |
| JP | 2009027637 A | 2/2009 |
| JP | 2009124429 A | 6/2009 |
| JP | 2011502369 A | 1/2011 |
| JP | 2012517766 A | 8/2012 |
| JP | 2013150294 A | 8/2013 |
| JP | 2014508442 A | 4/2014 |
| JP | 2014110638 A | 6/2014 |
| WO | 2014042269 A1 | 3/2014 |

OTHER PUBLICATIONS

International Search Report dated Aug. 14, 2015 in corresponding International Application PCT/CN2015/074923.
Extended European Search Report dated Sep. 27, 2017 in corresponding European Patent Application No. 15862787.7.
Notice of Reasons for Rejection, dated Sep. 21, 2018, in Japanese Application No. 2017528501 (16 pp.).

* cited by examiner

METHOD AND APPARATUS FOR MANAGING BODY DEVICE

CROSS-REFERENCE TO RELATED APPLICATIONS

This application is a continuation of International Application No. PCT/CN2015/074923, filed on Mar. 24, 2015, which claims priority to Chinese Patent Application No. 201410712732.3, filed on Nov. 29, 2014. The disclosures of the aforementioned applications are hereby incorporated by reference in their entireties.

TECHNICAL FIELD

The present invention relates to the communications field, and specifically, to a method and an apparatus for managing a body device.

BACKGROUND

With development of sciences and technologies, body devices are emerging endlessly. Body devices mainly include wearable devices and implantable devices. Common wearable devices include devices such as smart bands, smartglasses, and smartwatches. Implantable devices are devices implanted in a human body, for example, devices such as a cardiac pacemaker, a bionic eye, and a sensor. Some of these body devices are used for identity verification, some for illness treatment, some for controlling a remote device, and some for enhancing body performance.

In future, with improvement of living standards, every person is likely to carry hundreds of body devices. For these body devices to implement respective functions, every body device needs to be set. Therefore, how to simultaneously manage so many body devices is necessary to become an important concern of a device carrier.

SUMMARY

Embodiments of the present invention provide a method and an apparatus for managing a body device, which can simultaneously manage multiple body devices.

A first aspect of the embodiments of the present invention discloses a method for managing a body device, where the method includes:

obtaining, by a mobile personal station, an identifier of a body device;

obtaining, by the mobile personal station according to the identifier of the body device, a communication mode supported by the body device;

obtaining, by the mobile personal station, a body parameter and a location parameter that are of a user that carries the body device; and setting, by the mobile personal station, the body device according to the body parameter, the location parameter, and the communication mode supported by the body device.

With reference to the first aspect, in a first possible implementation manner of the first aspect, before the setting, by the mobile personal station, the body device according to the body parameter, the location parameter, and the communication mode supported by the body device, the method further includes:

determining, by the mobile personal station, a communication priority of the body device according to the communication mode supported by the body device;

obtaining, by the mobile personal station, an ambient parameter of the user that carries the body device; and the setting, by the mobile personal station, the body device according to the body parameter, the location parameter, and the communication mode supported by the body device specifically includes:

setting, by the mobile personal station, the body device according to the body parameter, the location parameter, the ambient parameter, and the communication priority.

With reference to the first aspect or the first possible implementation manner of the first aspect, in a second possible implementation manner of the first aspect, after the setting, by the mobile personal station, the body device according to the body parameter, the location parameter, and the communication mode supported by the body device, the method further includes:

obtaining, by the mobile personal station, data sent by the body device;

identifying, by the mobile personal station, an event type of the data;

performing, by the mobile personal station, matching between the event type of the data and a preset event; and when the event type of the data successfully matches a preset event, processing, by the mobile personal station, the data and sending an alert in a preset manner according to a processing result.

With reference to the second possible implementation manner of the first aspect, in a third possible implementation manner of the first aspect, the method further includes:

when the event type of the data does not match a preset event, obtaining, by the mobile personal station, a data reporting solution, where the data reporting solution is used to indicate whether to report after-preprocessing data or report before-preprocessing data to an information center; and sending, by the mobile personal station, the before-preprocessing data to the information center when the data reporting solution indicates reporting the before-preprocessing data to the information center, so that the information center processes the reported before-preprocessing data; or when the data reporting solution indicates reporting the after-preprocessing data to the information center, preprocessing, by the mobile personal station, the data and sending the after-preprocessing data to the information center, so that the information center processes the reported after-preprocessing data further.

With reference to the third possible implementation manner of the first aspect, in a fourth possible implementation manner of the aspect, after the obtaining a data reporting solution, the method further includes:

obtaining, by the mobile personal station, a network status of a network on which the mobile personal station is located; and the sending, by the mobile personal station, the before-preprocessing data to the information center when the data reporting solution indicates reporting the before-preprocessing data to the information center, so that the information center processes the reported data specifically includes:

sending, by the mobile personal station, the before-preprocessing data to the information center when the data reporting solution indicates reporting the before-preprocessing data to the information center and when the status of the network meets a preset network status requirement, so that the information center processes the data.

With reference to any one of the first aspect or the first to the fourth possible implementation manners of the first aspect, in a fifth possible implementation manner of the first aspect, after the setting, by the mobile personal station, the body device according to the body parameter, the location parameter, and the communication mode supported by the body device, the method further includes:

obtaining, by the mobile personal station, a network topology of the network on which the mobile personal station is located; and optimizing the network on which the mobile personal station is located, according to communication modes supported by body devices on the network on which the mobile personal station is located, a preset optimization algorithm, and the network topology.

With reference to any one of the first aspect or the first to the fifth possible implementation manners of the first aspect, in a sixth possible implementation manner, after the setting, by the mobile personal station, the body device according to the body parameter, the location parameter, and the communication mode supported by the body device, the method further includes:

detecting, by the mobile personal station, whether there is another mobile personal station within a preset range; and when another mobile personal station is detected, establishing a connection to the another mobile personal station, and sending data received by the mobile personal station to the second personal station, so that the another mobile personal station manages, when the mobile personal station runs out of power, the body device according to the data sent by the mobile personal station.

With reference to any one of the first aspect or the first to the sixth possible implementation manners of the first aspect, in a seventh possible implementation manner of the first aspect, after the setting, by the mobile personal station, the body device according to the body parameter, the location parameter, and the communication mode supported by the body device, the method further includes:

determining, by the mobile personal station according to the body parameter, a unique recognizable characteristic of the user that carries the mobile personal station;

establishing, by the mobile personal station, a security authentication manner with a gateway according to the unique recognizable characteristic of the user;

collecting, by the mobile personal station, a physiological characteristic of the user within a preset time by using the body device, and obtaining a collection result; and interacting, by the mobile personal station, with the gateway according to the collection result and the security authentication manner, for identity authentication on the user.

With reference to any one of the first aspect or the first to the seventh possible implementation manners of the first aspect, in an eighth possible implementation manner of the first aspect, after the setting, by the mobile personal station, the body device according to the body parameter, the location parameter, and the communication mode supported by the body device, the method further includes:

detecting, by the mobile personal station, strength of a radio signal of the body device;

determining, by the mobile personal station, a distance between the body device and the mobile personal station according to the strength of the radio signal of the body device; and when the distance is greater than a preset value, sending, by the mobile personal station, in a preset manner, an alert to the user that carries the mobile personal station.

With reference to any one of the first aspect or the first to the eighth possible implementation manners of the first aspect, in a ninth possible implementation manner of the first aspect, before the obtaining, by a mobile personal station, an identifier of a body device, the method further includes:

receiving, by the mobile personal station, a connection request sent by the body device, where the connection request includes the identifier of the body device;

detecting, by the mobile personal station, whether the identifier of the body device has already been stored; and establishing, by the mobile personal station, a connection to the body device when the identifier of the body device has already been stored; and the obtaining, by a mobile personal station, an identifier of a body device specifically includes:

obtaining, by the mobile personal station, the identifier of the body device that has been connected.

With reference to any one of the first aspect or the first to the ninth possible implementation manners of the first aspect, in a tenth possible implementation manner of the first aspect, the connection request further includes a parameter of the body device; and after the detecting, by the mobile personal station, whether the identifier of the body device has already been stored, the method further includes:

when the identifier of the body device has not yet been stored, checking, by the mobile personal station, whether the identifier of the body device is valid; and when the identifier of the body device is valid, establishing, by the mobile personal station, a connection to the body device, storing the identifier of the body device, and updating the body device list according to the parameter of the body device.

A second aspect of the embodiments of the present invention discloses an apparatus for managing a body device, where the apparatus includes:

an obtaining unit, configured to: obtain an identifier of the body device; traverse a body device list according to the identifier of the body device to obtain a communication mode supported by the body device; and obtain a body parameter and a location parameter that are of a user that carries the body device; and a setting unit, configured to set the body device according to the body parameter, the location parameter, and the communication mode supported by the body device that are obtained by the obtaining unit.

With reference to the second aspect, in a first possible implementation manner of the second aspect, the apparatus further includes a first determining unit;

the first determining unit is configured to determine a communication priority of the body device according to the communication mode supported by the body device that is obtained by the obtaining unit;

the obtaining unit is further configured to obtain an ambient parameter of the user that carries the body device; and the setting unit is specifically configured to set the body device according to the body parameter, the location parameter, and the ambient parameter that are obtained by the obtaining unit and according to the communication priority that is determined by the first determining unit.

With reference to the second aspect or the first possible implementation manner of the second aspect, in a second possible implementation manner of the second aspect, the apparatus further includes a recognition unit, a matching unit, and a first processing unit;

the obtaining unit is further configured to obtain data sent by the body device;

the recognition unit is configured to identify an event type of the data obtained by the obtaining unit;

the matching unit is configured to perform matching between the event type of the data and a preset event; and the first processing unit is configured to: when the event type of the data successfully matches a preset event, process the data and send an alert in a preset manner according to a processing result.

With reference to the second possible implementation manner of the second aspect, in a third possible implementation manner of the second aspect, the apparatus further includes a second processing unit and a sending unit;

the second processing unit is configured to obtain a data reporting solution when the event type of the data does not match a preset event, where the data reporting solution is used to indicate whether to report after-preprocessing data or report before-preprocessing data to an information center;

the sending unit is configured to send the before-preprocessing data to the information center when the data reporting solution indicates reporting the before-preprocessing data to the information center, so that the information center processes the reported before-preprocessing data; and the sending unit is further configured to: when the data reporting solution indicates reporting the after-preprocessing data to the information center, preprocess the data and send the after-preprocessing data to the information center, so that the information center processes the reported after-preprocessing data further.

With reference to the third possible implementation manner of the second aspect, in a fourth possible implementation manner of the second aspect, the obtaining unit is further configured to obtain a network status of a network on which the mobile personal station is located; and the sending unit is specifically configured to send the before-preprocessing data to the information center when the data reporting solution indicates reporting the before-preprocessing data to the information center and when the status of the network meets a preset network status requirement, so that the information center processes the data.

With reference to any one of the second aspect or the first to the fourth possible implementation manners of the second aspect, in a fifth possible implementation manner of the second aspect, the apparatus further includes a network optimization unit;

the obtaining unit is further configured to obtain a network topology of the network on which the mobile personal station is located; and the network optimization unit is specifically configured to optimize the network on which the mobile personal station is located, according to communication modes supported by body devices on the network on which the mobile personal station is located, a preset optimization algorithm, and the network topology.

With reference to any one of the second aspect or the first to the fifth possible implementation manners of the second aspect, in a sixth possible implementation manner of the second aspect, the apparatus further includes a first detection unit and a migration unit;

the first detection unit is configured to detect whether there is another mobile personal station within a preset range; and the migration unit is configured to: when another mobile personal station is detected, establish a connection to the another mobile personal station, and send data to the personal station, so that the another mobile personal station manages, when the mobile personal station runs out of power, the body device according to the data sent by the mobile personal station.

With reference to any one of the second aspect or the first to the sixth possible implementation manners of the second aspect, in a seventh possible implementation manner of the second aspect, the apparatus further includes a second determining unit, a negotiation unit, a collection unit, and an authentication unit;

the second determining unit is configured to determine, according to the body parameter obtained by the obtaining unit, a unique recognizable characteristic of the user that carries the mobile personal station;

the negotiation unit is configured to establish a security authentication manner with a gateway according to the unique recognizable characteristic of the user that is determined by the second determining unit;

the collection unit is configured to collect a physiological characteristic of the user within a preset time by using the body device, and obtain a collection result; and the authentication unit is configured to interact with the gateway according to the collection result obtained by the collection unit and according to the security authentication manner established by the negotiation unit, for identity authentication on the user.

With reference to any one of the second aspect or the first to the seventh possible implementation manners of the second aspect, in an eighth possible implementation manner of the second aspect, the apparatus further includes a second detection unit, a determining unit, and an alerting unit;

the second detection unit is configured to detect strength of a radio signal of the body device set by the setting unit;

the determining unit is configured to determine a distance between the body device and the mobile personal station according to the strength of the radio signal of the body device; and the alerting unit is configured to: when the distance is greater than a preset value, send, in a preset manner, an alert to the user that carries the mobile personal station.

With reference to any one of the second aspect or the first to the eighth possible implementation manners of the second aspect, in a ninth possible implementation manner of the second aspect, the apparatus further includes a receiving unit, a third detection unit, and a connection unit;

the receiving unit is configured to receive a connection request sent by the body device, where the connection request includes the identifier of the body device;

the third detection unit is configured to detect whether the identifier of the body device has already been stored;

the connection unit is configured to establish a connection to the body device when the identifier of the body device has already been stored; and the obtaining unit is configured to obtain the identifier of the body device that has been connected by the connection unit.

With reference to the ninth possible implementation manners of the second aspect, in a tenth possible implementation manner of the second aspect, the connection request further includes a parameter of the body device, and the apparatus further includes a check unit and an update unit;

the check unit is configured to: when the identifier of the body device has not yet been stored, check whether the identifier of the body device is valid; and the update unit is configured to: when the identifier of the body device is valid, establish a connection to the body device, store the identifier of the body device, and update the body device list according to the parameter of the body device.

It can be learned from the foregoing that, according to the method and the apparatus for managing a body device provided in the embodiments of the present invention, a mobile personal station obtains an identifier of a body device; the mobile personal station obtains, according to the identifier of the body device, a communication mode supported by the body device; the mobile personal station obtains a body parameter and a location parameter that are of a user; and the mobile personal station sets the body device according to the body parameter, the location parameter, and the communication mode supported by the body device. In this way, the body device can be set quickly, which facilitates management of the body device and improves user experience.

BRIEF DESCRIPTION OF DRAWINGS

To describe the technical solutions in the embodiments of the present invention more clearly, the following briefly describes the accompanying drawings required for describing the embodiments. Apparently, the accompanying drawings in the following description show merely some embodiments of the present invention, and a person of ordinary skill in the art may still derive other drawings from these accompanying drawings without creative efforts.

DESCRIPTION OF EMBODIMENTS

The following clearly describes the technical solutions in the embodiments of the present invention with reference to the accompanying drawings in the embodiments of the present invention. Apparently, the described embodiments are merely some but not all of the embodiments of the present invention. All other embodiments obtained by a person of ordinary skill in the art based on the embodiments of the present invention without creative efforts shall fall within the protection scope of the present invention.

As is for innovations and changes brought by automobiles, computers, the Internet, and smartphones, it is difficult to figure out a specific time taken from emergence to maturity and then to popular use of body devices by using simple production and sales volumes. However, body devices are obviously developing more quickly and are sure to bring extraordinary and incomparable impact on the future.

Body devices mainly include wearable devices and implantable devices. Common wearable devices include devices such as smart bands, smartglasses, and smartwatches. Implantable devices are devices implanted in a human body, for example, devices such as a cardiac pacemaker, a bionic eye, and a sensor. Some of these body devices are used for identity verification, some for illness treatment, some for controlling a remote device, and some for enhancing body performance.

In the long run, with the maturity and popularization of body devices, every individual person is likely to carry hundreds of body devices. With such a quantity of body devices, how to implement management becomes a headache for people. In view of this, the embodiments of the present invention provide a method and an apparatus for managing a body device, which can simultaneously manage multiple body devices, thereby resolving the foregoing headache.

Figure 1:
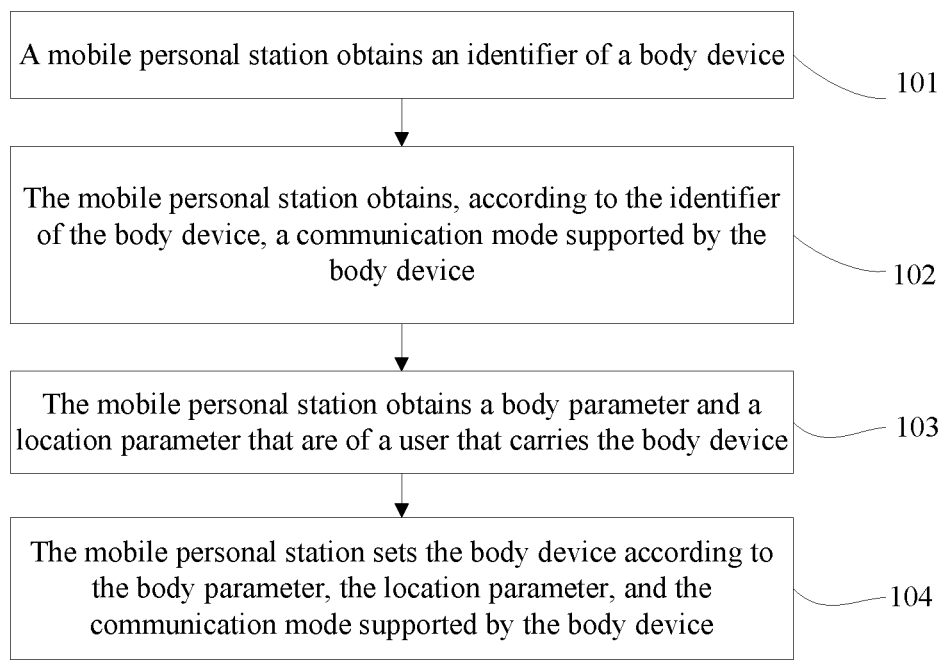
FIG. 1 is a flowchart of a method for managing a body device according to an embodiment of the present invention.

As shown in FIG. 1, FIG. 1 shows a method for managing a body device in an embodiment of the present invention. The method specifically includes step 101 to step 104.

101: A mobile personal station obtains an identifier of a body device.

The mobile personal station (MPS) is an apparatus that manages a body device. The mobile personal station may be regarded as one type of body device. The mobile personal station is small and portable for a user to carry. For example, the user may wear it on the wrist or tie it around the waist.

There are many manners to attach the mobile personal station to a human body, which are not listed one by one herein.

The identifier of the body device is used to uniquely identify the body device. For example, the identifier of the body device may be a factory-assigned serial number of the body device.

The user may register the body device with the MPS. The MPS may directly obtain the identifier of the body device according to registration information.

The body device may send a connection request to the MPS, where the connection request includes the identifier of the body device. The MPS may obtain the identifier of the body device according to the connection request.

The MPS may obtain all parameters of the device by using the identifier of the body device, such as the identifier, a name, a category, a type, a battery power status, a communication mode supported by the body device, and a communication priority that are of the body device. The identifier may be a serial number. The name may be a name specified by a manufacturer or may be a name specified by the user.

102: The mobile personal station obtains, according to the identifier of the body device, a communication mode supported by the body device.

The MPS may obtain the communication mode supported by the body device by using a body device list. The body device list may be set before factory delivery. The body device list includes some parameters or all parameters of body devices. The body device list may be constructed according to brands of the body devices or may be constructed according to types of the body devices. A specific construction manner of the body device list is not limited herein.

The MPS may obtain the communication mode supported by the body device according to the identifier network of the body device.

The mobile personal station traverses the body device list according to the identifier of the body device to obtain information about the body device from the body device list. Common information about a body device includes a communication mode supported by the body device, a communication priority, a battery power status, a device category, a device type, and the like.

Common communication modes include Bluetooth connection, Wi-Fi (Wireless Fidelity, Wireless Fidelity) connection, infrared ray connection, NFC (Near Field Communication, Near Field Communication) connection, terahertz connection, and the like.

103: The mobile personal station obtains a body parameter and a location parameter that are of a user that carries the body device.

The body parameter includes a physiological parameter of the human body and a behavior parameter of the human body. Common physiological parameters include a blood pressure, a heart rate, and the like. Common behavior parameters include a daily schedule of the user, an Internet-surfing time period of the user, and an Internet-surfing time point of the user, and the like.

The user is a user that carries the mobile personal station.

The location parameter includes a longitude, a latitude, and an altitude of a location of the user.

The location parameter may be obtained by using a location sensor. The location sensor may be a body device or may be a component of the MPS.

The MPS may obtain a current location of the user by using a map website on a network.

104: The mobile personal station sets the body device according to the body parameter, the location parameter, and the communication mode supported by the body device.

The mobile personal station functions like a gateway. The body device may be connected to the Internet by using the mobile personal station.

The mobile personal station sets, according to the communication mode supported by the body device, a communication mode for connecting with the body device. For example, the communication mode of the body device includes such modes as Wi-Fi, Bluetooth, NFC, and infrared ray. However, Wi-Fi has a highest priority in the communication modes of the body device, and therefore the mobile personal station sets the Wi-Fi connection mode of the body device as a default connection mode.

The mobile personal station sets a function of the body device according to the body parameter. For example, the body parameter includes a blood pressure or heart rate alarm threshold. If the body device has a function of detecting the blood pressure or the heart rate of the user, the mobile personal station sets the alarm threshold for the body device. When the body device detects that the blood pressure or the heart rate is greater than the alarm threshold, the body device sends an alert automatically, or the body device sends an alert to the user by using the mobile personal station.

In an embodiment of the present invention, when multiple body devices send threshold crossing alerts to the MPS, the MPS performs analysis and calculation to determine a cause for occurrence of the problem, and provides an emergency solution for the problem. The MPS may perform model training on received data to obtain a data analysis model.

It can be learned from the foregoing that, according to the method for managing a body device provided in this embodiment of the present invention, a mobile personal station obtains an identifier of a body device; the mobile personal station obtains, according to the identifier of the body device, a communication mode supported by the body device; the mobile personal station obtains a body parameter and a location parameter that are of a user that carries the body device; and the mobile personal station sets the body device according to the body parameter, the location parameter, and the communication mode supported by the body device. In this way, the body device can be set quickly, which facilitates management of the body device and improves user experience.

Figure 2:
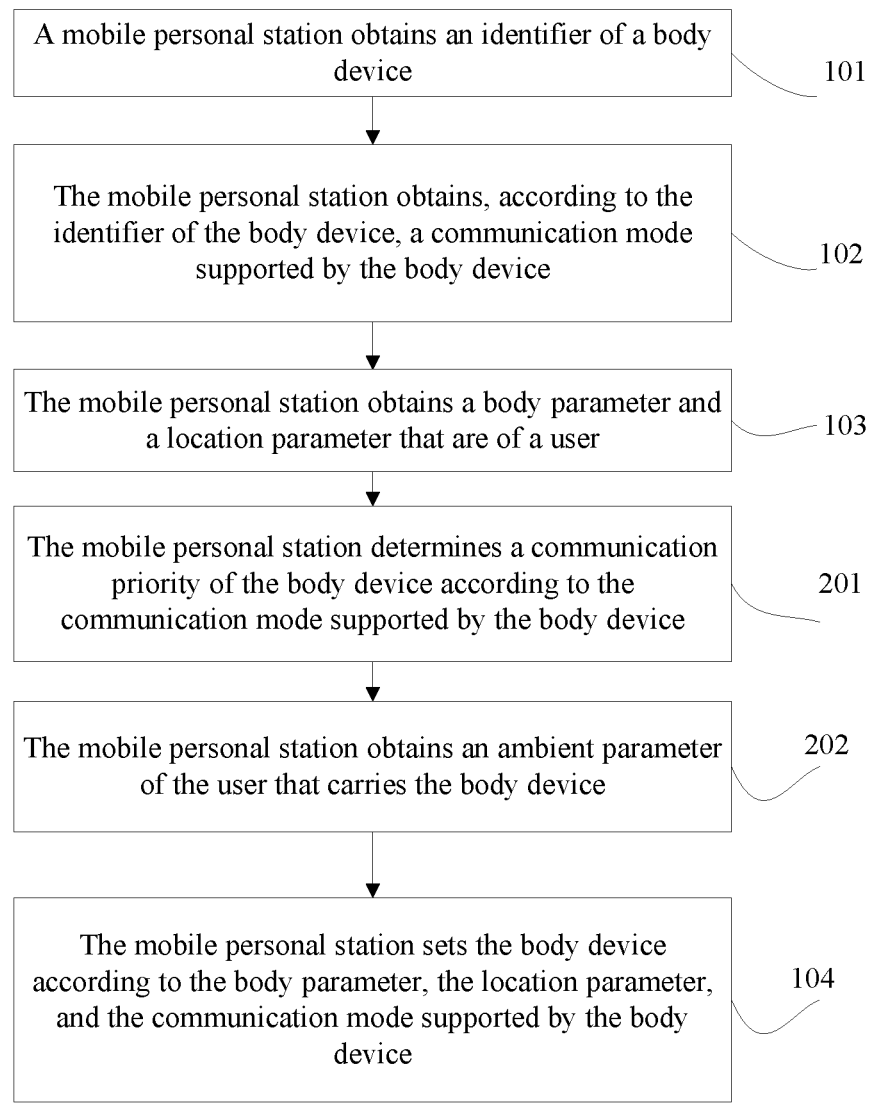
FIG. 2 is a flowchart of a method for managing a body device according to another embodiment of the present invention.

Optionally, as shown in FIG. 2, based on the foregoing embodiment, in another embodiment of the present invention, before step 104, the following steps are further included.

201: The mobile personal station determines a communication priority of the body device according to the communication mode supported by the body device.

The mobile personal station may determine the priority of the body device according to a behavior characteristic of the user. For example, if the user usually goes online to the Internet for videos, the mobile personal station may use Wi-Fi connection as a highest-priority communication mode.

The mobile personal station may determine the priority of the body device according to a power saving status. For example, if Bluetooth connection saves power the most, the Bluetooth connection communication mode is used as the highest-priority communication mode.

The communication priority means that, when the body device includes multiple communication modes, these communication modes have different priorities. For example, when wearable glasses have Wi-Fi, Bluetooth, infrared ray, and like communication modes, Wi-Fi has a highest communication priority, Bluetooth has a second highest communication priority, and infrared ray has a lowest communication priority. The setting of priorities may be specified by a manufacturer of the body device at factory delivery, or may be set according to frequencies at which the user uses the communication modes, or may be set by the MPS by means of calculation. The setting of communication priorities is not limited herein.

The MPS determines which communication mode is used to connect to the body device. For example, the MPS may use power consumption as a reference criterion for connection selection. For example, Wi-Fi is relatively power-consuming; therefore, the MPS may select a connection mode with lower power consumption such as Bluetooth for connection when the body device does not need to transmit a large amount of data, and the MPS may select Wi-Fi with higher power consumption for connection when the body device needs to transmit a large amount of data.

202: The mobile personal station obtains an ambient parameter of the user that carries the body device.

The ambient parameter includes an air humidity, an air temperature, an ultraviolet ray strength, a carbon dioxide concentration, an air quality, and the like.

Step 104 that the mobile personal station sets the body device according to the body parameter, the location parameter, and the communication mode supported by the body device specifically includes:

the mobile personal station sets the body device according to the body parameter, the location parameter, the ambient parameter, and the communication priority.

The body parameter includes the physiological parameter of the human body and the behavior parameter of the human body.

The mobile personal station uses the physiological parameter of the human body, the behavior parameter of the human body, the location parameter, and the ambient parameter, and the communication priority as input to perform calculation according to a preset model, and sets the body device according to a calculation result. The preset model may be set in advance, or may be trained according to historical data by using a machine training algorithm. The historical data may be obtained from a network or may be accumulated gradually.

It can be learned from the foregoing that, according to the method for managing a body device provided in this embodiment of the present invention, the mobile personal station sets the body device according to the body parameter, the location parameter, the ambient parameter, and the communication priority. In this way, the body device can be set and managed more accurately.

Figure 3A:
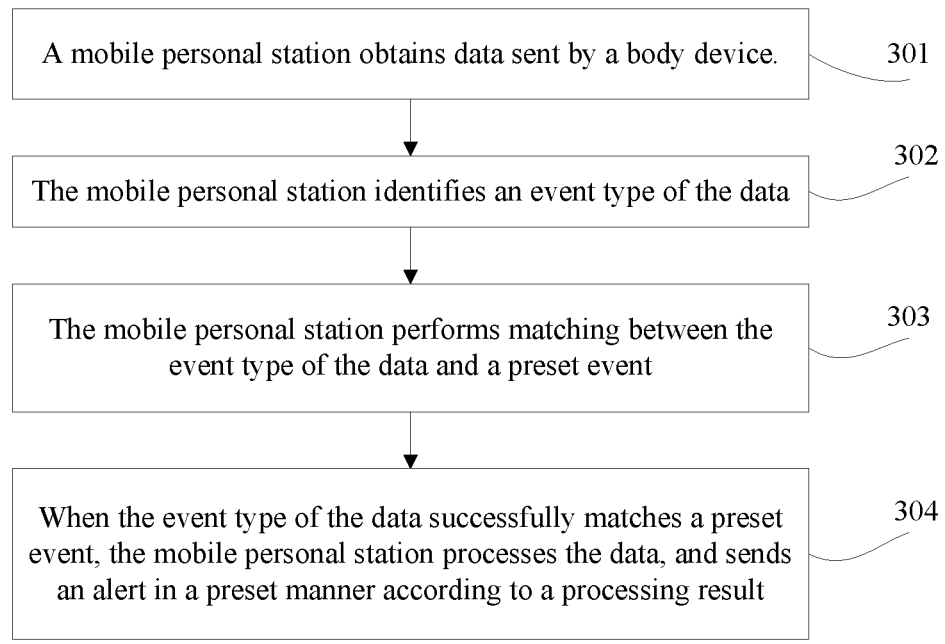
FIG. 3a is a flowchart of a method for managing a body device according to another embodiment of the present invention.

Optionally, as shown in FIG. 3a, on the basis of the foregoing embodiment, the technical solution of the present invention further includes the following steps. After the mobile personal station sets the body device according to the body parameter, the location parameter, and the communication mode supported by the body device, the following is further included.

301: The mobile personal station obtains data sent by the body device.

The data is data collected by the body device. The data includes the physiological parameter of the human body, the behavior parameter of the human body, the location parameter, and the ambient parameter. For example, the physiological parameter of the human body includes parameters such as a heart rate and a blood pressure. The behavior parameter of the human body includes parameters such as an Internet-surfing time point and an Internet-surfing time period of the user, and an amount of calories eaten by the user every day. The ambient parameter includes an air pollution index, a temperature, a humidity, a carbon dioxide concentration, and the like of an environment that the user is in. The location parameter includes a latitude and a longitude of a location of the user, an altitude of the location, a name of the location, and the like.

302: The mobile personal station identifies an event type of the data.

The event type may be classified according to types of body devices. For example, the event type includes heart rate data, blood pressure data, humidity data, data of the user's Internet-surfing time period, data of the user's Internet-surfing time point, and the like.

Alternatively, the event type may be classified into an emergency event type and a non-emergency event type. Such event type classification is made according to an emergency degree of the data to the user. If the data is critical to the user's life or property, the data belongs to the emergency event type. If the data is used for model training, which is used for analysis of a living habit or working habit of the user, the data belongs to the non-emergency event type.

Alternatively, the event type may also be classified into a lightweight type and a heavyweight type. Such event type classification is made based on a processing capability of the MPS. Data belongs to lightweight data if a conclusion can be drawn from analysis made by the MPS. Data beyond a computing capability of the MPS belongs to heavyweight data, and the MPS needs to send the heavyweight data to an information center for analysis. The information center may be a cloud computing platform.

303: The mobile personal station performs matching between the event type of the data and a preset event.

The mobile personal station may set a preset event list according to an emergency status of an event, or the computing capability of the mobile personal station, or types of body devices. For example, the preset event list may include a heart rate data type and a blood pressure data type.

304: When the event type of the data successfully matches a preset event, the mobile personal station processes the data, and sends an alert in a preset manner according to a processing result.

After the mobile personal station processes the data, reporting the data or after-processing data to the information center may be further included, so that the information center performs model training or deep analysis according to the received data.

When the event type of the data successfully matches a preset event, it indicates that the data is an emergency event or an event within the processing capability of the MPS. The mobile personal station analyzes the data and sends an alert to the user according to an analysis result. For example, when the body device sends, to the mobile personal station, a blood pressure or a heart rate that exceeds a preset value, the mobile personal station needs to analyze the blood pressure or the heart rate, then performs determining with reference to data sent by another body device, and then sends an alert to the user. For example, the mobile personal station receives data sent by the body device. The data includes that the blood pressure of the human body exceeds a preset value, that the heart rate of the human body is higher than a second preset value, and that a posture sensor detects that the user is in a fall-down state. In this case, the mobile personal station performs analysis with reference to the foregoing data to determine that the abnormal blood pressure and heart rate are caused by a fall-down, and the mobile personal station alerts the user to make an emergency call or directly makes an emergency call for the user.

The mobile personal station has a data analysis capability, and performs functions such as cause analysis, solution computing, and user alerting by comprehensively using data of all body devices. For example, when the mobile personal station receives data, the data is a status that the body device uses Wi-Fi. After the body device is not using Wi-Fi for more than half an hour, the mobile personal station actively changes a connection mode, for example, changing Wi-Fi connection to Bluetooth connection, to save power for the body device.

Figure 3B:
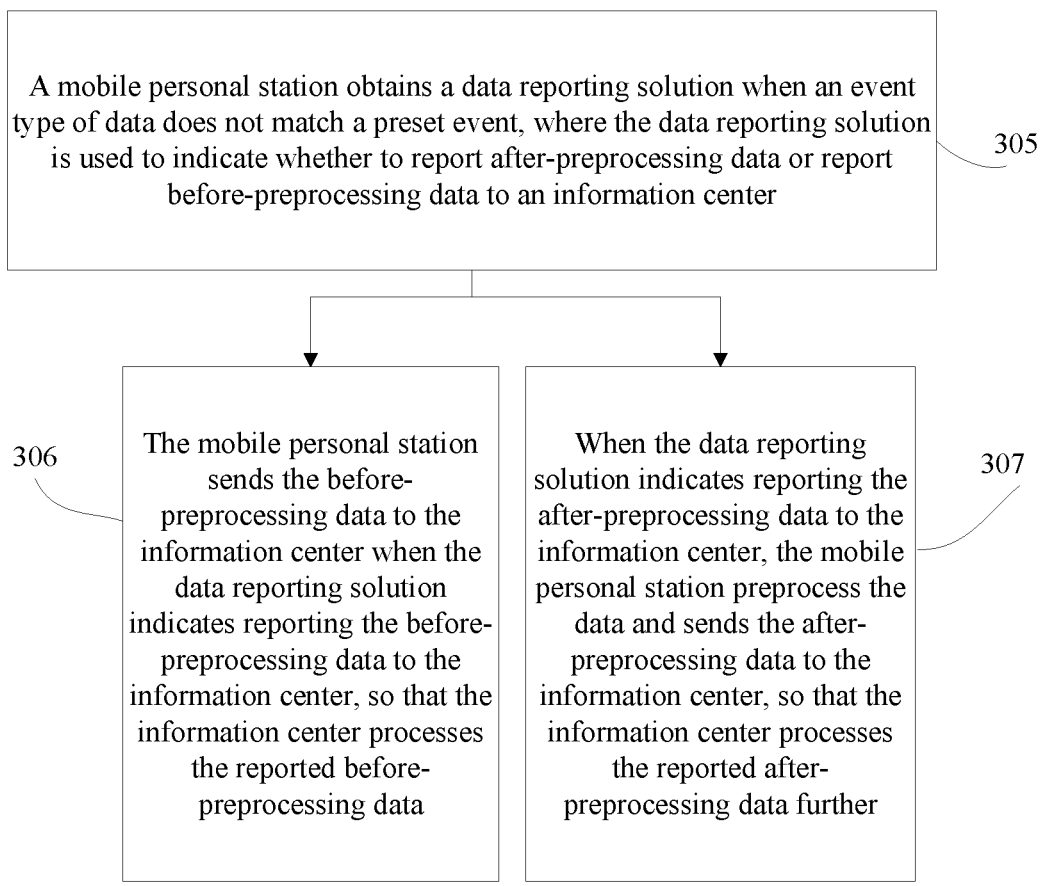
FIG. 3b is a flowchart of a method for managing a body device according to another embodiment of the present invention.

Optionally, as shown in FIG. 3b, on the basis of FIG. 3a, the technical solution of the present invention further includes the following steps:

305: The mobile personal station obtains a data reporting solution when the event type of the data does not match a preset event, where the data reporting solution is used to indicate whether to report after-preprocessing data or report before-preprocessing data to an information center.

The information center may analyze the reported data in depth, and confirm or correct a preprocessing result of the mobile personal station.

When the event type of the data does not match a preset event, it indicates that the data is not an emergency event or that the data is relatively complex and goes beyond the computing capability of the MPS. However, the MPS preprocesses the data. The preprocessing includes: collecting the data, computing the data, integrating the data, and the like.

That the mobile personal station preprocesses the data means that the mobile personal station performs several analysis and determining operations or obtains a preliminary determining result, according to the data. Then the information center performs analysis and correction according to the preliminary determining result or the before-preprocessing data, or verifies or confirms the analysis and determining provided by the mobile personal station.

306: The mobile personal station sends the before-preprocessing data to the information center when the data reporting solution indicates reporting the before-preprocessing data to the information center, so that the information center processes the reported before-preprocessing data.

307: When the data reporting solution indicates reporting the after-preprocessing data to the information center, the mobile personal station preprocess the data and sends the after-preprocessing data to the information center, so that the information center processes the reported after-preprocessing data further.

Figure 3C:
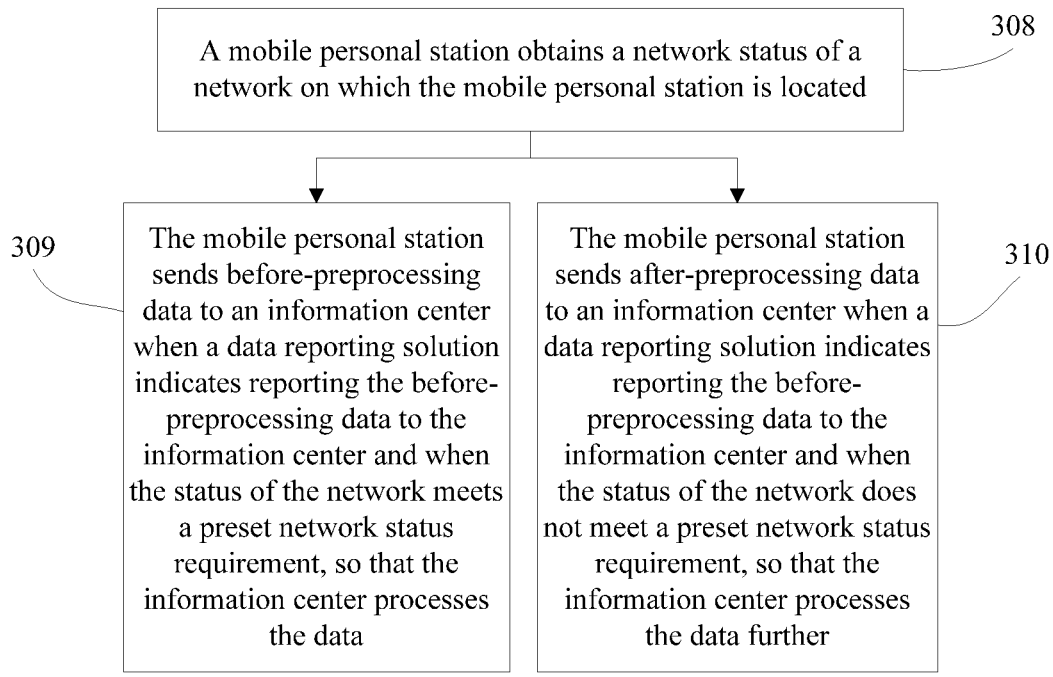
FIG. 3c is a flowchart of a method for managing a body device according to another embodiment of the present invention.

Optionally, as shown in FIG. 3c, on the basis of FIG. 3b, the technical solution of the present invention further includes the following steps.

After the obtaining a data reporting solution, the following is further included.

308: The mobile personal station obtains a network status of a network on which the mobile personal station is located.

The network status indicates whether the network is in a congestion state. For example, determining may be performed by calculating a proportion of packets successfully sent within a preset time period.

That the mobile personal station sends the before-preprocessing data to the information center when the data reporting solution indicates reporting the before-preprocessing data to the information center, so that the information center processes the reported before-preprocessing data specifically includes:

309: The mobile personal station sends the before-preprocessing data to the information center when the data reporting solution indicates reporting the before-preprocessing data to the information center and when the status of the network meets a preset network status requirement, so that the information center processes the data.

The preset network status requirement may be measured according to a proportion of packets successfully sent within a preset time period. For example, the preset network status requirement may be so set that 95% packets are successfully sent within a preset time period.

The mobile personal station has a data analysis capability, and performs functions such as scenario analysis, solution computing, and user alerting by comprehensively using data of all body devices. For example, the mobile personal station receives data sent by a posture sensor, and analyzes the data to determine that the user is swimming. Then the mobile personal station analyzes a water temperature, a water depth, and a possible risk at the location of the user, and sends an alert to the user.

When the network operates very smoothly and meets the network status requirement, because the information center has a very strong computing capability, the mobile personal station may perform several analysis and determining operations or obtain a preliminary determining result, according to the data. Then the information center performs analysis and correction according to the preliminary determining result or the raw data, or verifies or confirms the analysis and determining provided by the mobile personal station. The information center may be a cloud computing platform.

Optionally, based on the foregoing embodiment, the following step is further included.

310: The mobile personal station sends the after-preprocessing data to the information center when the data reporting solution indicates reporting the before-preprocessing data to the information center and when the status of the network does not meet the preset network status requirement, so that the information center processes the data further.

It can be learned from the foregoing that, according to the method for managing a body device provided in this embodiment of the present invention, the mobile personal station obtains data sent by the body device; the mobile personal station identifies an event type of the data; the mobile personal station performs matching between the event type of the data and a preset event; and when the event type of the data successfully matches a preset event, the mobile personal station processes the data, and sends an alert to the user according to a processing result; or when the event type of the data does not match a preset event, the mobile personal station preprocesses the data, and obtains a data reporting solution, where the data reporting solution is used to indicate whether to report after-preprocessing data or report before-preprocessing data to an information center, so that the information center analyzes the reported data in depth and confirms or corrects a preprocessing result of the mobile personal station. In this way, the mobile personal station processes the data according to the matching result and the data reporting solution, and working efficiency of the mobile personal station is improved.

Figure 4:
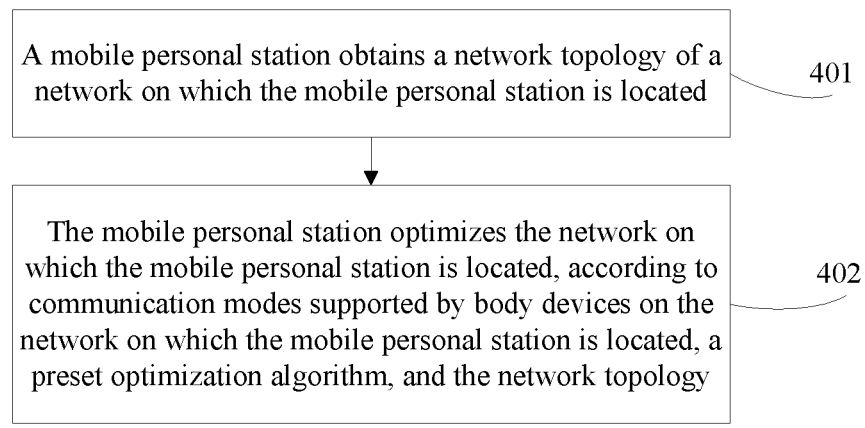
FIG. 4 is a flowchart of a method for managing a body device according to another embodiment of the present invention.

Optionally, as shown in FIG. 4, on the basis of the foregoing embodiments, the technical solution of the present invention further includes the following steps.

After the mobile personal station sets the body device according to the body parameter, the location parameter, and the communication mode supported by the body device, the following is further included.

401: The mobile personal station obtains a network topology of the network on which the mobile personal station is located.

The network topology refers to a connection relationship between the mobile personal station and body devices on the network.

402: The mobile personal station optimizes the network on which the mobile personal station is located, according to communication modes supported by body devices on the network on which the mobile personal station is located, a preset optimization algorithm, and the network topology.

There are many body devices connected to the network. The body devices are connected to the network in different manners, and the body devices are not all working at same time. There are many choices for the body device whether to connect to the mobile personal station via one hop or multiple hops. Therefore, the mobile personal device may determine the connection relationship with the body devices according to the network topology, and then optimize the connection relationship according to the communication modes supported by the body devices, communication priorities, and the preset optimization algorithm, so that all the body devices on the entire network implement their respective functions in a more power-saving state.

The preset optimization algorithm includes a table-driven routing protocol, an on-demand routing protocol, or the like. For example, a typical representative of the table-driven routing protocol is the DSDV (Destination-Sequenced Distance-Vector Routing) protocol. A typical representative of the on-demand routing protocol is the Dynamic Source Routing protocol (DSR, Dynamic Source Routing).

It can be learned from the foregoing that, according to the method for managing a body device provided in this embodiment of the present invention, the mobile personal station obtains a network topology of a network on which the mobile personal station is located; the mobile personal station optimizes the network on which the mobile personal station is located, according to communication modes of body devices on the network on which the mobile personal station is located, a preset optimization algorithm, and the network topology. The mobile personal station obtains a connection relationship with the body devices within the network by using the network topology, and optimizes the connection relationship with the body devices according to the communication modes and communication priorities that are of the body devices, and the preset optimization algorithm. In this way, it is more convenient for the user to manage the body devices, and overall power consumption of the body devices can be reduced, so that the body devices are more power-saving, and battery performance of the body devices is improved.

Figure 5:
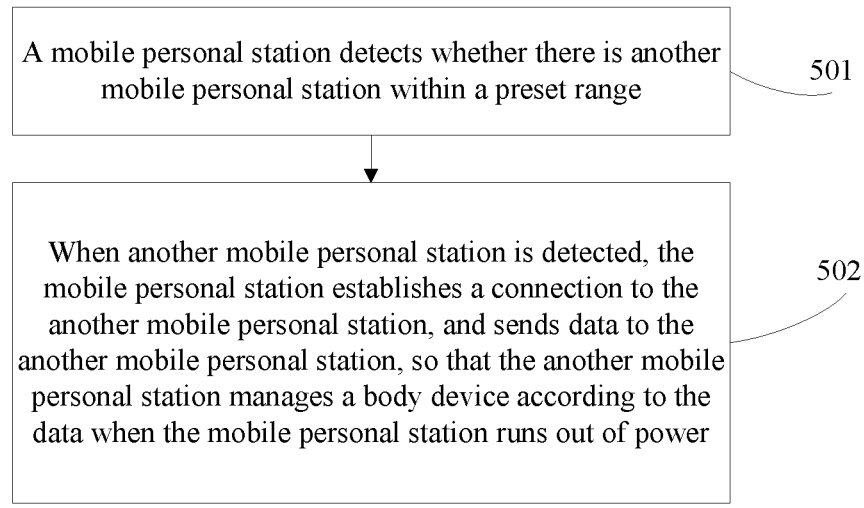
FIG. 5 is a flowchart of a method for managing a body device according to another embodiment of the present invention.

Optionally, as shown in FIG. 5, on the basis of the foregoing embodiments, the technical solution of the present invention further includes the following steps.

After the mobile personal station sets the body device according to the body parameter, the location parameter, and the communication mode supported by the body device, the following is further included.

501: The mobile personal station detects whether there is another mobile personal station within a preset range.

The MPS is a hotspot. The mobile personal station may detect, within the preset range, whether there is a network covered by another mobile personal station. When the mobile personal station detects a network covered by another mobile personal station, it indicates that there is another mobile personal station in the preset range.

502: When another mobile personal station is detected, the mobile personal station establishes a connection to the another mobile personal station, and sends data received by the mobile personal station to the second mobile personal station, so that the another mobile personal station manages, when the mobile personal station runs out of power, the body device according to the data sent by the mobile personal station.

The data that is received by the mobile personal station and that is sent by the mobile personal station to the second mobile personal station may be all data received by the mobile personal station, or may be the data received from the body device.

When the mobile personal station runs out of power or the mobile personal station is unable to connect to the Internet, the mobile personal station may establish the connection to the another mobile personal station, and send, to the another mobile personal station, the data received by the mobile personal station. The data may be sent to the mobile personal station by the body device.

When the mobile personal station runs out of power, the mobile personal station sends the data to the another mobile personal station, to implement migration of a management function, so that the another mobile personal station manages the body device according to the data.

When unable to connect to the Internet, the mobile personal station may regard the another mobile personal station as a gateway to connect to the Internet by using the network of the another mobile personal station.

It can be learned from the foregoing that, according to the method for managing a body device provided in this embodiment of the present invention, the mobile personal station detects whether there is another mobile personal station within a preset range; when another mobile personal station is detected, the mobile personal station establishes a connection to the another mobile personal station, and sends data to the second personal station, so that the another mobile personal station manages the body device according to the data when the mobile personal station runs out of power. The mobile personal station migrates the data to the another mobile personal station, which ensures continuity in management of the body device.

Figure 6:
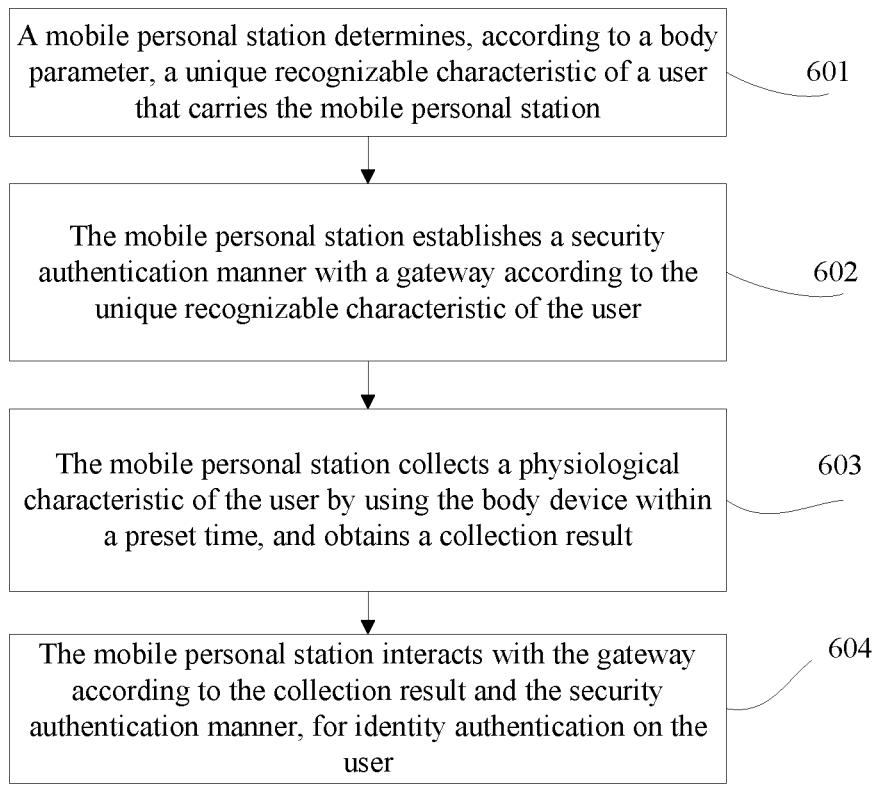
FIG. 6 is a flowchart of a method for managing a body device according to another embodiment of the present invention.

Optionally, as shown in FIG. 6, on the basis of the foregoing embodiments, the technical solution of the present invention further includes the following steps.

After the mobile personal station sets the body device according to the body parameter, the location parameter, and the communication mode supported by the body device, the following is further included.

601: The mobile personal station determines, according to the body parameter, a unique recognizable characteristic of the user that carries the mobile personal station.

The unique recognizable characteristic of the user includes at least one of the following: a fingerprint, an iris, or a DNA (Deoxyribonucleic acid, deoxyribonucleic acid).

602: The mobile personal station establishes a security authentication manner with a gateway according to the unique recognizable characteristic of the user.

For example, it is assumed that the unique recognizable characteristic of the user is a fingerprint, and the mobile personal station may negotiate with the gateway to use the fingerprint of the user as the security authentication manner.

The gateway may be a gateway at home, or may be a gateway in office, or may be a gateway in an automobile. For example, it is assumed that the gateway is a gateway in office, and the mobile personal station may submit a physiological characteristic of the user to the gateway in office, for identity authentication. A scenario of the gateway is not limited herein.

603: The mobile personal station collects a physiological characteristic of the user within a preset time by using the body device, and obtains a collection result.

The preset time may be 3 seconds or may be 10 seconds. A specific preset time is not limited herein.

The collecting a physiological characteristic of the user includes collecting a DNA, fingerprint or iris sample. How the collection is performed is not limited herein. For example, fallen hair or skin of may be collected as a DNA sample of the user.

604: The mobile personal station interacts with the gateway according to the collection result and the security authentication manner, so that identity authentication on the user can be performed.

The mobile personal station may send the collection result to the gateway, so that the gateway performs authentication according to the collection result, and then the gateway sends an authentication result to the mobile personal station. For example, the collection result may be a fingerprint, or may be a DNA, or may be a combination thereof.

In an embodiment of the present invention, the MPS has capabilities of obtaining and analyzing physiological data of a human body. For example, the MPS may be configured for security authentication based on a physiological characteristic of a human body. For example, because the MPS is configured for body device management, the MPS is often carried along with the user. Therefore, the MPS may submit physiological information of the user to a home gateway for authentication when the user arrives home or leaves home, so as to achieve automatic door unlocking or locking. Similarly, when the user comes to an automobile, the MPS may submit a physiological characteristic of the user to a gateway in the automobile for authentication by the automobile. When the authentication is successful, the automobile may, for example, automatically start up. There are many similar embodiments in which the MPS performs collection and then a gateway performs authentication, which are not listed one by one herein.

It can be learned from the foregoing that, according to the method for managing a body device provided in this embodiment of the present invention, the mobile personal station establishes a security authentication manner with a gateway according to a unique recognizable characteristic of the user; the mobile personal station collects a physiological characteristic of the user within a preset time by using the body device that has been connected, and obtains a collection result; and the mobile personal station interacts with the gateway according to the collection result, for identity authentication on the user. The mobile personal station implements identity authentication on the user by using the physiological characteristic of the user collected by the body device, making the user's life more convenient.

Figure 7:
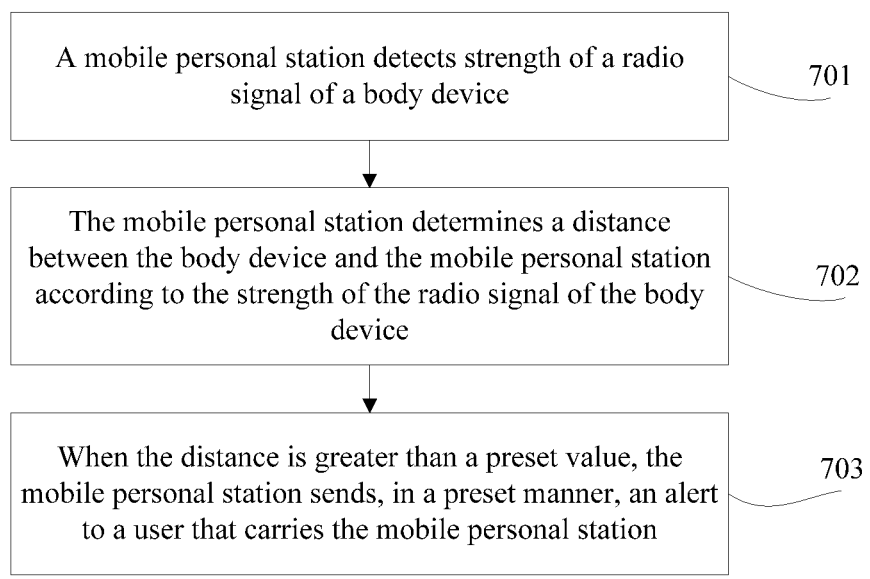
FIG. 7 is a flowchart of a method for managing a body device according to another embodiment of the present invention.

Optionally, as shown in FIG. 7, on the basis of the foregoing embodiments, the technical solution of the present invention further includes the following steps.

After the mobile personal station sets the body device according to the body parameter, the location parameter, and the communication mode supported by the body device, the following is further included.

701: The mobile personal station detects strength of a radio signal of the body device.

After the mobile personal station establishes a connection to and sets the body device, the mobile personal station can manage the body device. To implement real-time interaction with the body device, the mobile personal station detects the strength of the radio signal of the body device, to ensure normal proceeding of the interaction.

702: The mobile personal station determines a distance between the body device and the mobile personal station according to the strength of the radio signal of the body device.

The mobile personal station establishes a radio connection to the body device, where the strength of the radio signal varies with the distance between the mobile personal station and the body device. The mobile personal station may determine the distance between the mobile personal station and the body device according to the strength of the radio signal.

703: When the distance is greater than a preset value, the mobile personal station sends, in a preset manner, an alert to the user that carries the mobile personal station.

The preset value is set according to a safe range of the user, which may be a default value or may be user-adjustable. A common preset value may be 5 meters, 10 meters, or the like, and the preset value is not limited herein.

In an embodiment of the present invention, the MPS may determine a relative distance between the MPS and the body device by detecting the strength of the radio signal of the body device. When it is found that the strength of the radio signal of the body device decreases progressively to below the specified threshold, the MPS may send an alert to the user by means of, for example, a sound or vibration. For example, the alert may include a body device that the user forgets to carry, a location of the body device, and a distance between the body device and the user. The location of the body device may be estimated by using a transmission direction of an electromagnetic wave. The distance between the body device and the user may be estimated by using the strength of the radio signal.

In an embodiment of the present invention, a wireless locator card may be placed in a wallet. When the MPS detects that strength of a signal of the wireless locator card is less than a preset value, the MPS may alert, by means of vibration or a sound, the user that the wallet is lost.

It can be learned from the foregoing that, according to the method for managing a body device provided in this embodiment of the present invention, the mobile personal station determines a distance between the body device and the mobile personal station according to strength of a radio signal of the body device; and the mobile personal station sends an alert to the user in a preset manner when the distance is greater than a preset value. The mobile personal station determines the distance between the body device and the mobile personal station according to the strength of the radio signal of the body device, which facilitates convenience for the user to manage the body device.

Figure 8:
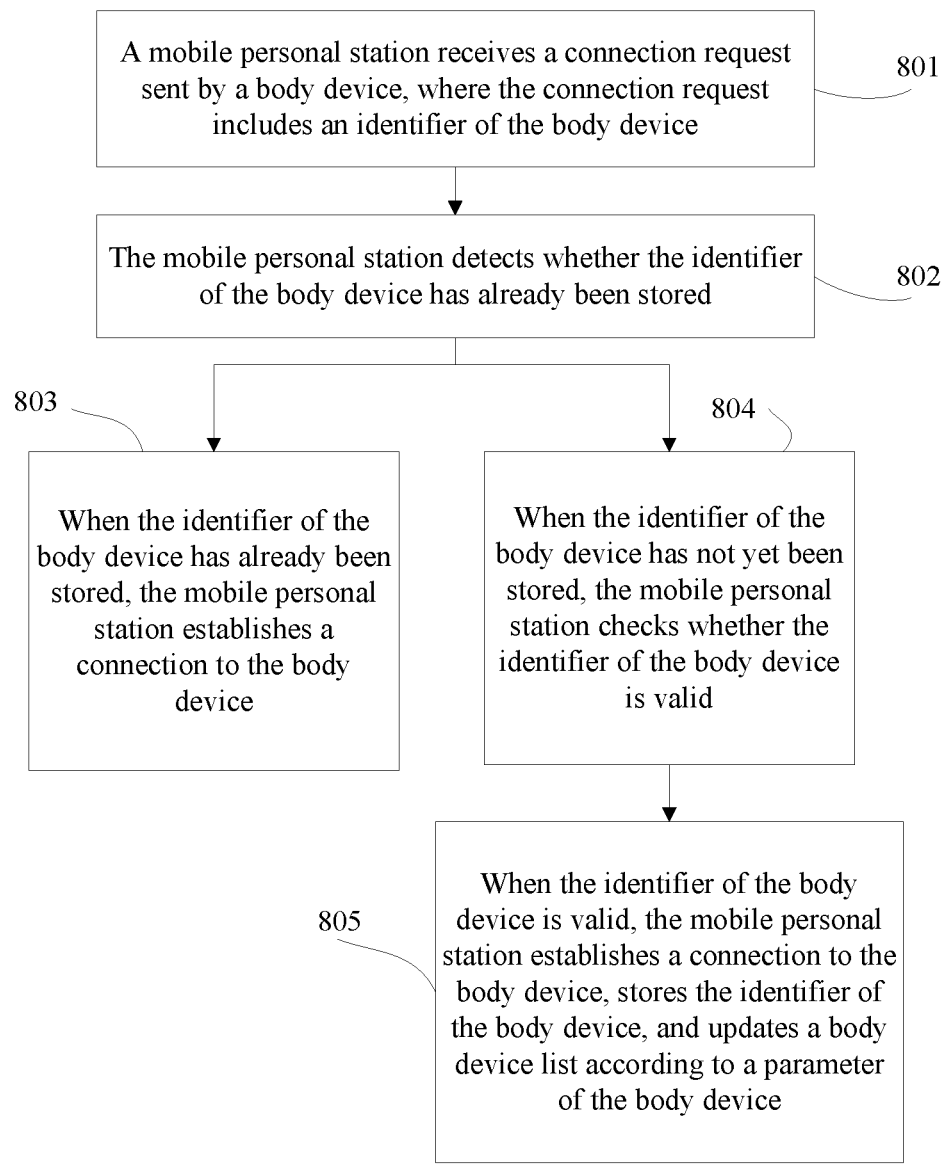
FIG. 8 is a flowchart of a method for managing a body device according to another embodiment of the present invention.

Optionally, as shown in FIG. 8, on the basis of the foregoing embodiments, the technical solution of the present invention further includes the following steps.

801: The mobile personal station receives a connection request sent by the body device, where the connection request includes the identifier of the body device.

The identifier of the body device may be a factory-assigned serial number.

Alternatively, the mobile personal station may search for a body device within a preset distance to obtain an identifier of the body device, and send a connection request to the body device to establish a connection to the body device. For example, the preset distance may be 1 meter, 2 meters, 5 meters, or even 10 meters. The preset distance is not limited herein.

802: The mobile personal station detects whether the identifier of the body device has already been stored.

If the body device established a connection to the mobile personal station in the past, the identifier of the body device has been stored by the mobile personal station. If the body device did not establish a connection to the mobile personal station in the past, the identifier of the body device has not been stored by the mobile personal station.

803: When the identifier of the body device has already been stored, the mobile personal station establishes a connection to the body device.

That the mobile personal station obtains the identifier of the body device specifically includes: the mobile personal station obtains the identifier of the body device that has been connected.

If the identifier of the body device has already been stored, it indicates that the body device established a connection to the mobile personal station in the past. Therefore, a connection may be directly established this time.

Optionally, as shown in FIG. 8, the technical solution of the present invention further includes the following steps, where the connection request further includes a parameter of the body device.

804: When the identifier of the body device has not yet been stored, the mobile personal station checks whether the identifier of the body device is valid.

Checking whether the identifier is valid may be performed by determining whether the identifier is in compliance with a naming rule of a manufacturer of the body device, or may be performed by confirming, by the user, whether the identifier is set by the user. For example, if it is determined, according to the identifier, that the identifier is a serial number of the manufacturer, it is determined that the identifier is in compliance with the naming rule of the manufacturer. If it is determined that the identifier is a manmade name, an alert is sent to the user for the user to determine whether the identifier is named by the user, and whether the identifier of the body device is valid is determined according to the determining of the user.

Checking whether the identifier is valid further includes: traversing a body device list to determine whether the body device is added by the user to the body device list, to prevent a device of another user from establishing a connection to the device of the user. For example, to manage the body device, the user may enter the identifier of the body device to the MPS in advance before the body device establishes the connection to the MPS, so that the MPS performs validity check on the body device according to the body device list when the MPS establishes the connection to the body device.

When performing the validity check on the identifier, the MPS may alert the user so that the user manually checks validity of the body device.

805: When the identifier of the body device is valid, the mobile personal station establishes a connection to the body device, stores the identifier of the body device, and updates the body device list according to the parameter of the body device.

Because it is the first time that the body device establishes a connection to the mobile personal station, the body device list may be updated according to the parameter of the body device. Updating the body device list includes: adding the parameter of the body device to the body device list.

It can be learned from the foregoing that, according to the method for managing a body device provided in this embodiment of the present invention, the mobile personal station checks whether the identifier of the body device has already been stored; and when the identifier of the body device has already been stored, the mobile personal station establishes a connection to the body device; or when the identifier of the body device has not yet been stored, the mobile personal station checks whether the identifier of the body device is valid, and when the identifier of the body device is valid, the mobile personal station establishes a connection to the body device, and updates the body device list according to a parameter of the body device. The mobile personal station establishes the connection according to the identifier of the body device, which facilitates setting of the body device.

Figure 9:
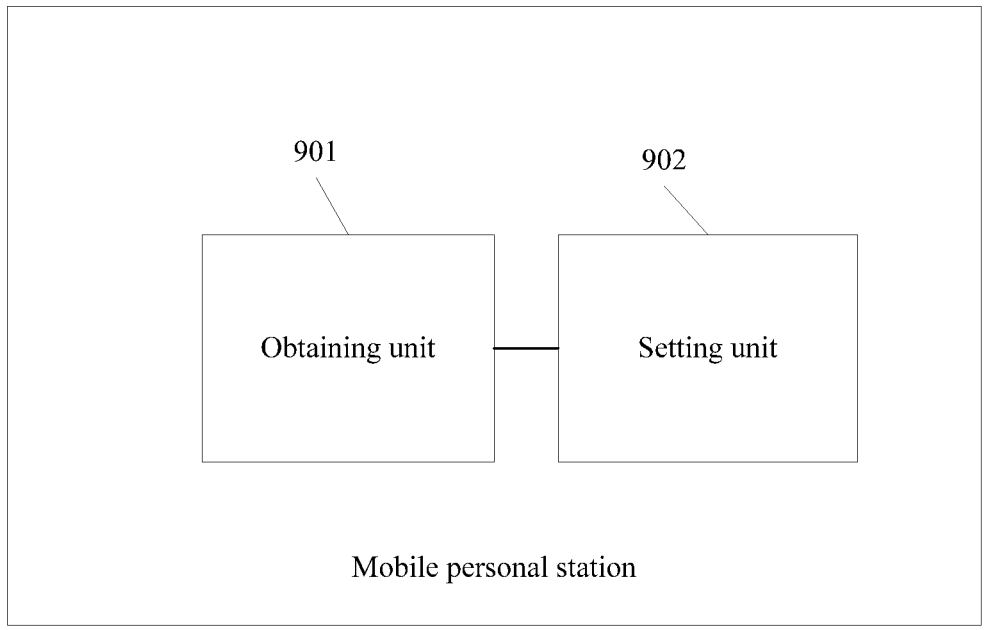
FIG. 9 is a structural diagram of an apparatus for managing a body device according to an embodiment of the present invention.

As shown in FIG. 9, FIG. 9 shows an apparatus for managing a body device, that is, a mobile personal station, in an embodiment of the present invention. The mobile personal station may be a smart terminal, such as a smart band, a smart necklace, or smartglasses, or may be an application program on a smart terminal, which is not limited herein. The mobile personal station 90 is configured to execute the method for managing a body device described in the foregoing embodiments. The mobile personal station 90 includes an obtaining unit 901 and a setting unit 902.

The obtaining unit 901 is configured to obtain an identifier of a body device.

The identifier may be a factory-assigned device serial number or the like, which is not limited herein.

The obtaining unit 901 is further configured to traverse a body device list according to the identifier of the body device, to obtain a communication mode supported by the body device.

The obtaining unit 901 is further configured to obtain a body parameter and a location parameter that are of a user that carries the body device.

The body parameter includes a physiological parameter of the human body and a behavior parameter of the human body.

The location parameter includes parameters such as a latitude, a longitude and an altitude that are of a location of the human body.

The setting unit 902 is configured to set the body device according to the body parameter, the location parameter, and the communication mode supported by the body device that are obtained by the obtaining unit 901.

It can be learned from the foregoing that, according to the apparatus for managing a body device provided in this embodiment of the present invention, a mobile personal station obtains an identifier of a body device; the mobile personal station obtains, according to the identifier of the body device, a communication mode supported by the body device; the mobile personal station obtains a body parameter and a location parameter that are of a user that carries the body device; and the mobile personal station sets the body device according to the body parameter, the location parameter, and the communication mode supported by the body device. In this way, the body device can be set quickly, which facilitates management of the body device and improves user experience.

Figure 10:
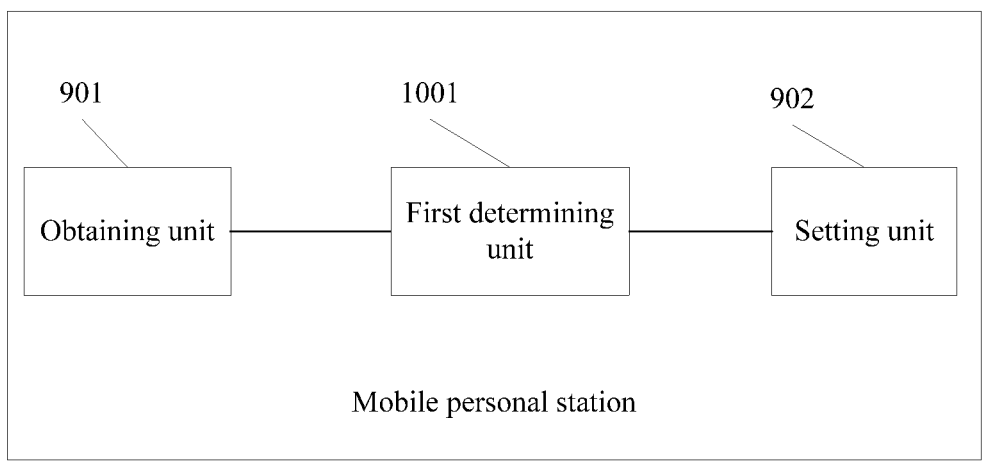
FIG. 10 is a structural diagram of an apparatus for managing a body device according to another embodiment of the present invention.

Optionally, as shown in FIG. 10, based on the foregoing apparatus provided in the foregoing apparatus embodiment, the apparatus further includes a first determining unit 1001.

The first determining unit 1001 is configured to determine a communication priority of the body device according to the communication mode supported by the body device.

For specifics of the determining a communication priority of the body device, reference is made to the descriptions of the method embodiments.

The obtaining unit 901 is further configured to obtain an ambient parameter of the user that carries the body device.

The ambient parameter includes parameters such as an air humidity, a temperature, an ultraviolet ray strength, and an air quality of an environment that the human body is in.

The setting unit 902 is specifically configured to set the body device according to the body parameter, the location parameter, and the ambient parameter that are obtained by the obtaining unit 901 and according to the communication priority.

It can be learned from the foregoing that, according to the apparatus for managing a body device provided in this embodiment of the present invention, the mobile personal station sets the body device according to the body parameter, the location parameter, the ambient parameter, and the communication priority. In this way, the body device can be set and managed more accurately.

Optionally, based on the foregoing apparatus, the apparatus further includes a recognition unit 1101, a matching unit 1102, and a first processing unit 1103.

The obtaining unit 901 is further configured to obtain data sent by the body device.

The recognition unit 1101 is configured to identify an event type of the data.

The matching unit 1102 is configured to perform matching between the event type of the data and a preset event.

The first processing unit 1103 is configured to: when the event type of the data successfully matches a preset event, process the data and send an alert in a preset manner according to a processing result.

Figure 11:
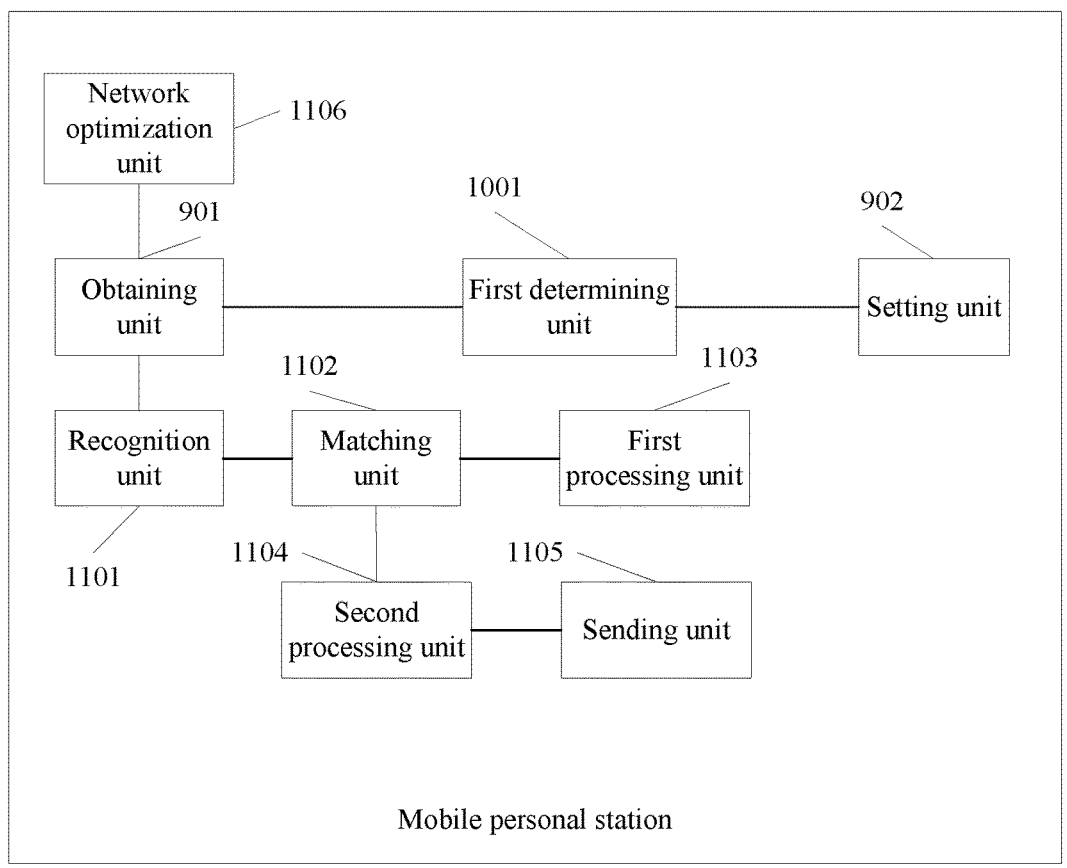
FIG. 11 is a structural diagram of an apparatus for managing a body device according to another embodiment of the present invention.

Optionally, as shown in FIG. 11, based on the foregoing apparatus, the apparatus further includes a second processing unit 1104 and a sending unit 1105.

The second processing unit 1104 is configured to obtain a data reporting solution when the event type of the data does not match a preset event, where the data reporting solution is used to indicate whether to report after-preprocessing data or report before-preprocessing data to an information center.

The information center analyzes the reported data in depth, and confirms or corrects a preprocessing result of the mobile personal station.

The sending unit 1105 is configured to send the before-preprocessing data to the information center when the data reporting solution indicates reporting the before-preprocessing data to the information center, so that the information center processes the reported before-preprocessing data.

The sending unit 1105 is further configured to: when the data reporting solution indicates reporting the after-preprocessing data to the information center, preprocess the data and send the after-preprocessing data to the information center, so that the information center processes the reported after-preprocessing data further.

Optionally, based on the foregoing apparatus:

the obtaining unit 901 is further configured to obtain a network status of a network on which the mobile personal station is located; and the sending unit 1105 is specifically configured to send the before-preprocessing data to the information center when the data reporting solution indicates reporting the before-preprocessing data to the information center and when the status of the network meets a preset network status requirement, so that the information center processes the data.

Optionally, based on the foregoing apparatus, the sending unit 1105 is further specifically configured to send the after-preprocessing data to the information center when the data reporting solution indicates reporting the before-preprocessing data to the information center and when the status of the network does not meet the preset network status requirement, so that the information center processes the data further.

It can be learned from the foregoing that, according to the apparatus for managing a body device provided in this embodiment of the present invention, the mobile personal station obtains data sent by the body device; the mobile personal station identifies an event type of the data; the mobile personal station performs matching between the event type of the data and a preset event; and when the event type of the data successfully matches a preset event, the mobile personal station processes the data, and sends an alert to the user according to a processing result; or when the event type of the data does not match a preset event, the mobile personal station preprocesses the data, and obtains a data reporting solution, where the data reporting solution is used to indicate whether to report after-preprocessing data or report before-preprocessing data to an information center, so that the information center analyzes the reported data in depth and confirms or corrects a preprocessing result of the mobile personal station. In this way, the mobile personal station processes the data according to the matching result and the data reporting solution, and working efficiency of the mobile personal station is improved.

Optionally, based on the foregoing apparatus, the apparatus further includes a network optimization unit 1106.

The obtaining unit 901 is further configured to obtain a network topology of the network on which the mobile personal station is located.

The network optimization unit 1106 is specifically configured to: optimize the network on which the mobile personal station is located, according to communication modes supported by body devices on the network on which the mobile personal station is located, a preset optimization algorithm, and the network topology.

It can be learned from the foregoing that, according to the apparatus for managing a body device provided in this embodiment of the present invention, the mobile personal station obtains a network topology of a network on which the mobile personal station is located; the mobile personal station optimizes the network on which the mobile personal station is located, according to communication modes supported by body devices on the network on which the mobile personal station is located, a preset optimization algorithm, and the network topology. The mobile personal station obtains a connection relationship with the body devices within the network by using the network topology, and optimizes the connection relationship with the body devices according to the communication modes and communication priorities that are of the body devices, and the preset optimization algorithm. In this way, it is more convenient for the user to manage the body devices, and overall power consumption of the body devices can be reduced, so that the body devices are more power-saving, and battery performance of the body devices is improved.

Figure 12:
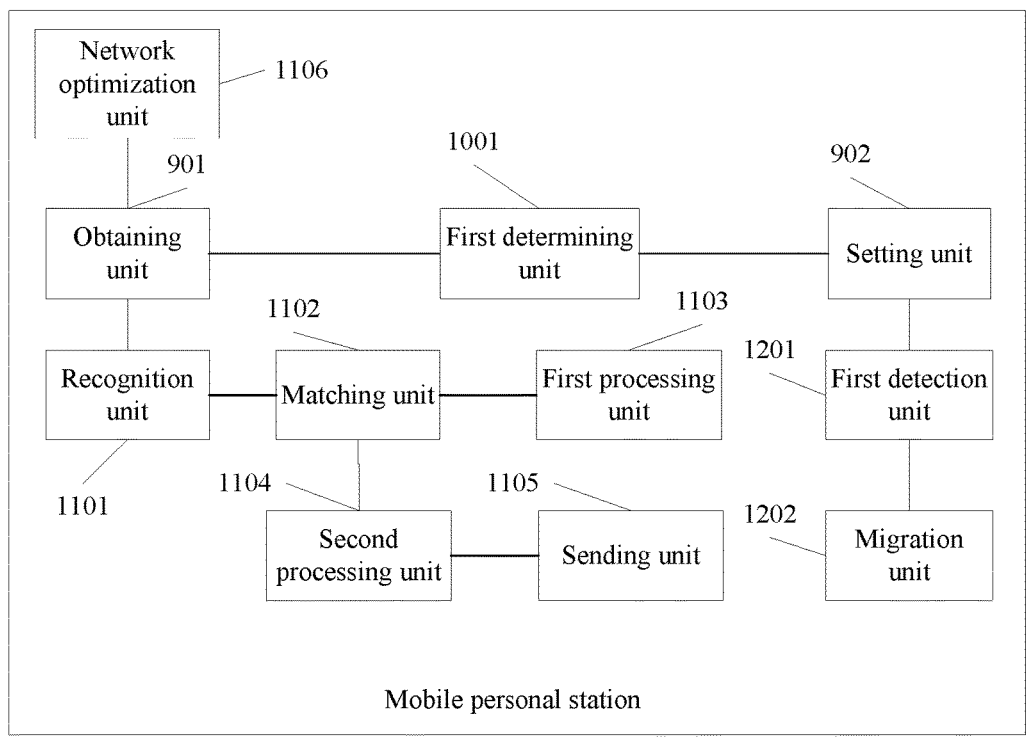
FIG. 12 is a structural diagram of an apparatus for managing a body device according to another embodiment of the present invention.

Optionally, as shown in FIG. 12, based on the foregoing apparatus embodiment, the apparatus further includes a first detection 1201 and a migration unit 1202.

The first detection unit 1201 is configured to detect whether there is another mobile personal station within a preset range.

The first detection unit 1201 is connected to the setting unit 902.

The migration unit 1202 is configured to: when another mobile personal station is detected, establish a connection to the another mobile personal station, and send data received by the mobile personal station to the second personal station, so that the another mobile personal station manages the body device according to the data when the mobile personal station runs out of power.

It can be learned from the foregoing that, according to the apparatus for managing a body device provided in this embodiment of the present invention, the mobile personal station detects whether there is another mobile personal station within a preset range; when another mobile personal station is detected, the mobile personal station establishes a connection to the another mobile personal station, and sends data to the second personal station, so that the another mobile personal station manages the body device according to the data when the mobile personal station runs out of power. The mobile personal station migrates the data to the another mobile personal station, which ensures continuity in management of the body device.

Figure 13:
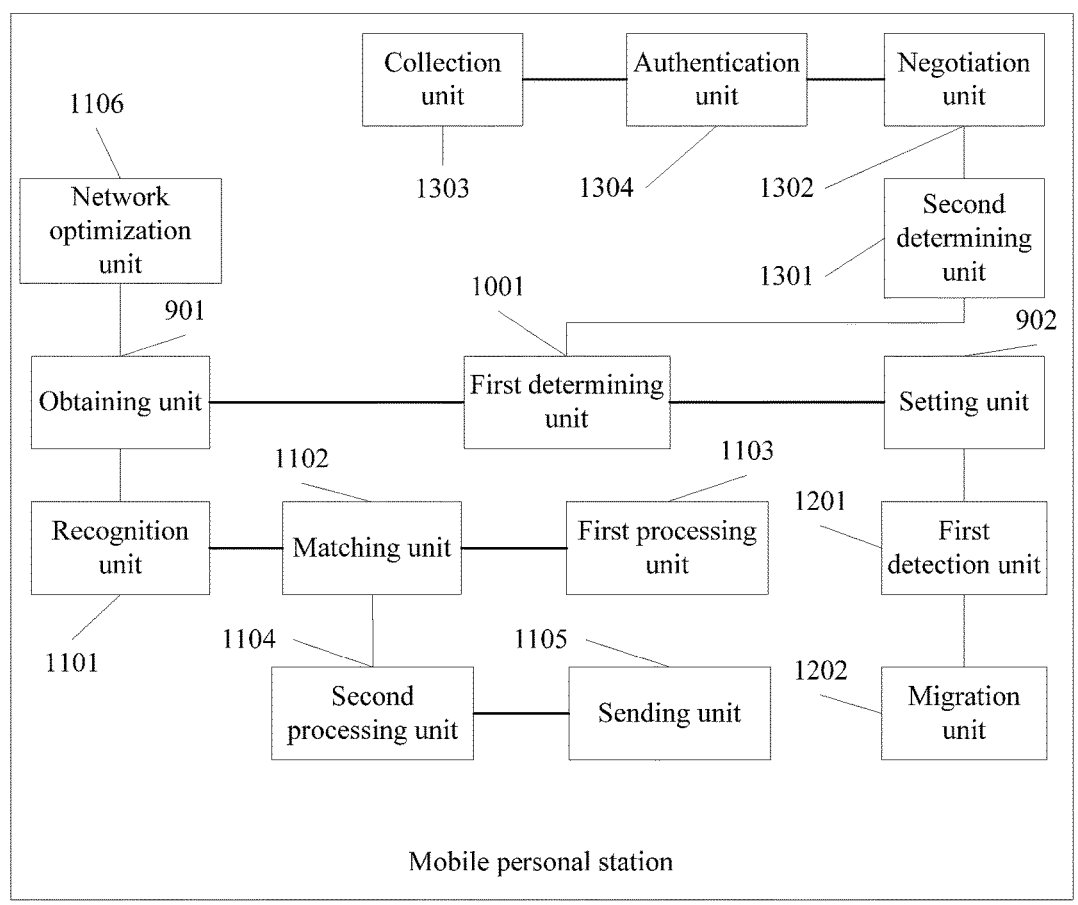
FIG. 13 is a structural diagram of an apparatus for managing a body device according to another embodiment of the present invention.

Optionally, as shown in FIG. 13, based on the foregoing apparatus embodiment, the apparatus further includes a second determining unit 1301, a negotiation unit 1302, a collection unit 1303, and an authentication unit 1304.

The second determining unit 1301 is configured to determine, according to the body parameter obtained by the obtaining unit 901, a unique recognizable characteristic of the user that carries the mobile personal station;

The second determining unit 1301 is connected to the obtaining unit 901.

The negotiation unit 1302 is configured to establish a security authentication manner with a gateway according to the unique recognizable characteristic of the user.

The collection unit 1303 is configured to collect a physiological characteristic of the user within a preset time by using a body device, and obtain a collection result.

The authentication unit 1304 is configured to interact with the gateway according to the collection result obtained by the collection unit 1303 and according to the security authentication manner established by the negotiation unit 1302, for identity authentication on the user.

Figure 14:
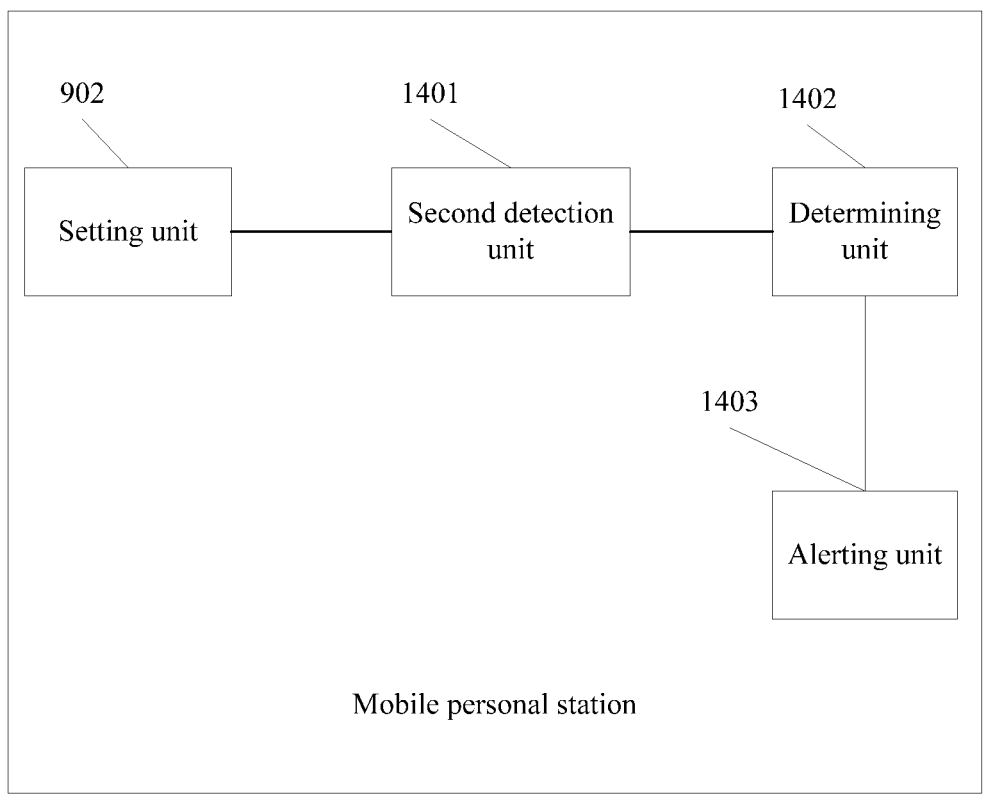
FIG. 14 is a structural diagram of an apparatus for managing a body device according to another embodiment of the present invention.

Optionally, as shown in FIG. 14, based on the foregoing apparatus embodiment, the apparatus further includes a second detection unit 1401, a determining unit 1402, and an alerting unit 1403.

The second detection unit 1401 is configured to detect strength of a radio signal of the body device set by the setting unit 902.

The second detection unit 1401 is connected to the setting unit 902.

The determining unit 1402 is configured to determine a distance from the body device to the mobile personal station according to the strength of the radio signal of the body device.

The alerting unit 1403 is configured to: when the distance is greater than a preset value, send, in a preset manner, an alert to the user that carries the mobile personal station.

It can be learned from the foregoing that, according to the apparatus for managing a body device provided in this embodiment of the present invention, the mobile personal station establishes a security authentication manner with a gateway according to a unique recognizable characteristic of the user; the mobile personal station collects a physiological characteristic of the user within a preset time by using the body device that has been connected, and obtains a collection result, and the mobile personal station interacts with the gateway according to the collection result, for identity authentication on the user. The mobile personal station implements identity authentication on the user by using the physiological characteristic of the user collected by the body device, making the user's life more convenient.

Figure 15:
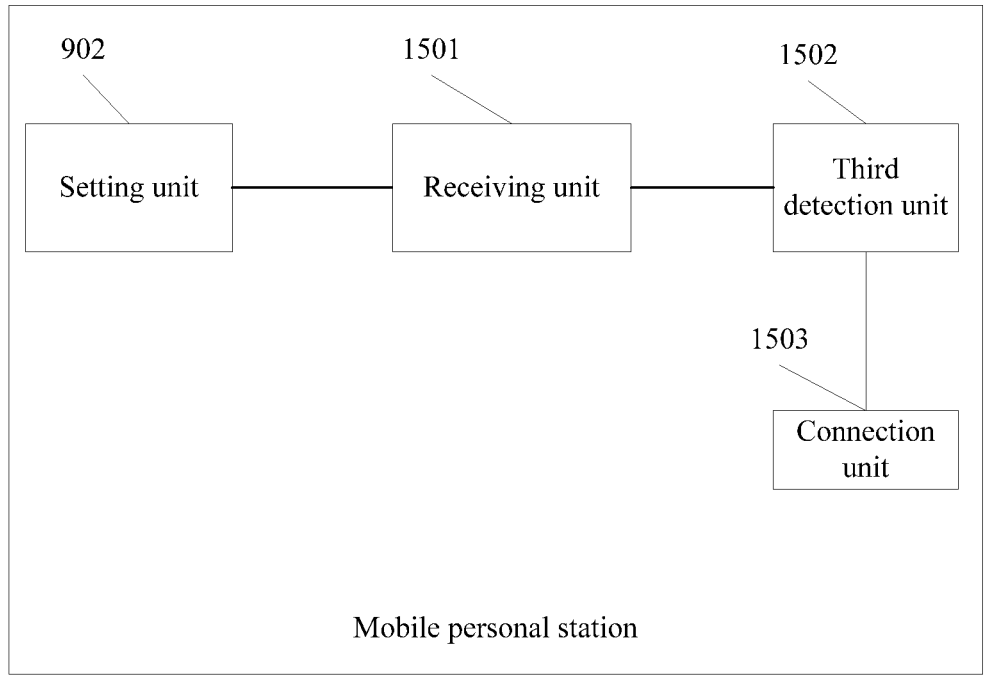
FIG. 15 is a structural diagram of an apparatus for managing a body device according to another embodiment of the present invention.

Optionally, as shown in FIG. 15, based on the foregoing apparatus embodiment, the apparatus further includes a receiving unit 1501, a third detection unit 1502, and a connection unit 1503.

The receiving unit 1501 is configured to receive a connection request sent by the body device, where the connection request includes the identifier of the body device.

The receiving unit 1501 is connected to the setting unit 902.

The third detection unit 1502 is configured to detect whether the identifier of the body device has already been stored.

The connection unit 1503 is configured to establish a connection to the body device when the identifier of the body device has already been stored.

The obtaining unit 901 is configured to obtain the identifier of the body device that has been connected by the connection unit 1503.

It can be learned from the foregoing that, according to the apparatus for managing a body device provided in this embodiment of the present invention, the mobile personal station determines a distance between the body device and the mobile personal station according to strength of a radio signal of the body device; and the mobile personal station sends an alert to the user in a preset manner when the distance is greater than a preset value. The mobile personal station determines the distance between the body device and the mobile personal station according to the strength of the radio signal of the body device, which facilitates convenience for the user to manage the body device.

Figure 16:
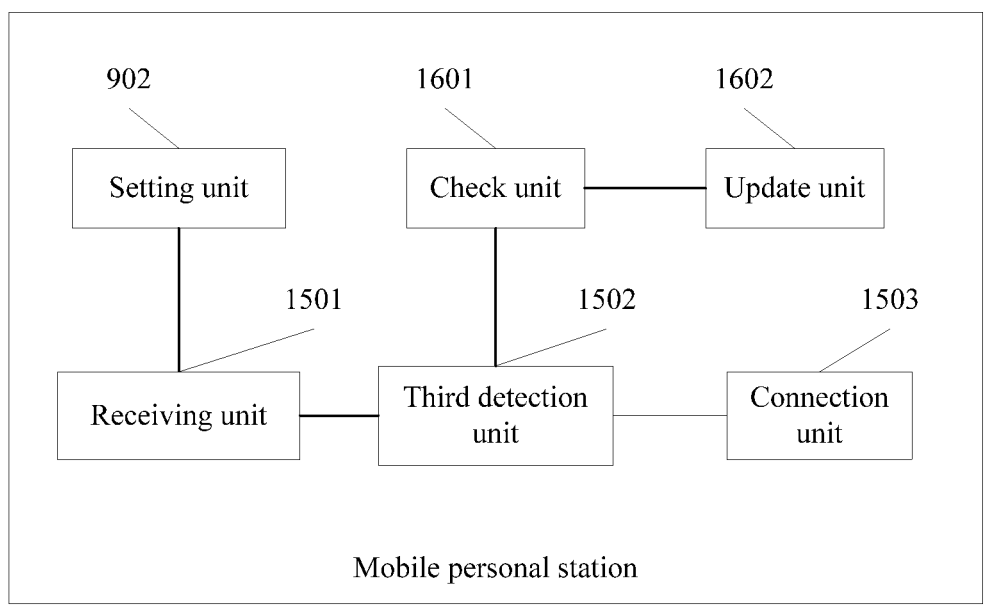
FIG. 16 is a structural diagram of an apparatus for managing a body device according to another embodiment of the present invention.

Optionally, as shown in FIG. 16, based on the foregoing apparatus embodiment, the apparatus further includes a check unit 1601 and an update unit 1602. The connection request further includes a parameter of the body device.

The check unit 1601 is configured to: when the identifier of the body device has not yet been stored, check whether the identifier of the body device is valid.

The update unit 1602 is configured to: when the identifier of the body device is valid, establish a connection to the body device, store the identifier of the body device, and update a body device list according to the parameter of the body device.

It can be learned from the foregoing that, according to the apparatus for managing a body device provided in this embodiment of the present invention, the mobile personal station checks whether the identifier of the body device has already been stored; and when the identifier of the body device has already been stored, the mobile personal station establishes a connection to the body device; or when the identifier of the body device has not yet been stored, the mobile personal station checks whether the identifier of the body device is valid, and when the identifier of the body device is valid, the mobile personal station establishes a connection to the body device, and updates the body device list according to a parameter of the body device. The mobile personal station establishes the connection according to the identifier of the body device, which facilitates setting of the body device.

Figure 17:
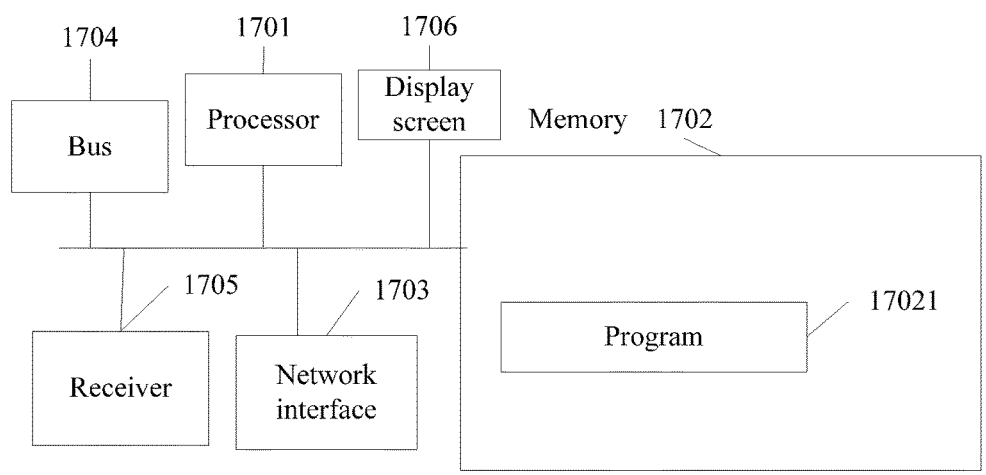
FIG. 17 is a structural diagram of an apparatus for managing a body device according to another embodiment of the present invention.

FIG. 17 shows a structure of an apparatus for managing a body device provided in another embodiment of the present invention, including at least one processor 1701 (for example, a CPU), a memory 1702, at least one network interface 1703, at least one communications bus 1704, at least one receiver 1705, and a display screen 1706, where the communications bus 1704 is configured to implement communication connections between these apparatuses. The processor 1701 is configured to execute an executable module, for example, a computer program, stored in the memory 1702. The memory 1702 may include a high-speed random access memory (RAM: Random Access Memory), or may further include a non-volatile memory (non-volatile memory), for example, at least an eMMC (Embedded Multi Media Card, embedded multimedia card) memory. The at least one network interface 1703 (which may be wired or wireless) is configured to implement a communication connection between the network device and at least one other network element, where the Internet, a wide area network, a local area network, a metropolitan area network, or the like may be used. The terminal is configured to execute the method described in the foregoing embodiments.

In some implementation manners, the memory 1702 stores a program 17021, and the program 17021 can be executed by the processor 1701. The program includes:

obtaining an identifier of a body device;

obtaining, according to the identifier of the body device, a communication mode supported by the body device;

obtaining a body parameter and a location parameter that are of a user that carries the body device; and setting the body device according to the body parameter, the location parameter, and the communication mode supported by the body device.

Optionally, before the setting the body device according to the body parameter, the location parameter, and the communication mode supported by the body device, the following is further included:

determining a communication priority of the body device according to the communication mode supported by the body device;

obtaining an ambient parameter of the user that carries the body device; and the setting the body device according to the body parameter, the location parameter, and the communication mode supported by the body device specifically includes:

setting the body device according to the body parameter, the location parameter, the ambient parameter, and the communication priority.

Optionally, after the setting the body device according to the body parameter, the location parameter, and the communication mode supported by the body device, the following is further included:

obtaining data sent by the body device;

identifying an event type of the data;

performing matching between the event type of the data and a preset event; and when the event type of the data successfully matches a preset event, processing the data, and sending an alert in a preset manner according to a processing result.

Optionally, the method further includes:

obtaining a data reporting solution when the event type of the data does not match a preset event, where the data reporting solution is used to indicate whether to report after-preprocessing data or report before-preprocessing data to an information center; and sending the before-preprocessing data to the information center when the data reporting solution indicates reporting the before-preprocessing data to the information center, so that the information center processes the reported before-preprocessing data; or when the data reporting solution indicates reporting the after-preprocessing data to the information center, preprocessing the data and sending the after-preprocessing data to the information center, so that the information center processes the reported after-preprocessing data further.

Optionally, before the sending the data to the information center, so that the information center processes the data, the following is further included:

obtaining a network status of a network on which the mobile personal station is located; and the sending the before-preprocessing data to the information center when the data reporting solution indicates reporting the before-preprocessing data to the information center, so that the information center processes the reported data specifically includes:

sending the before-preprocessing data to the information center when the data reporting solution indicates reporting the before-preprocessing data to the information center and when the status of the network meets a preset network status requirement, so that the information center processes the data.

Optionally, after the setting the body device according to the body parameter, the location parameter, and the communication mode supported by the body device, the following is further included:

obtaining a network topology of the network on which the mobile personal station is located; and optimizing the network on which the mobile personal station is located, according to communication modes supported by body devices on the network on which the mobile personal station is located, a preset optimization algorithm, and the network topology.

Optionally, after the setting the body device according to the body parameter, the location parameter, and the communication mode supported by the body device, the following is further included:

detecting whether there is another mobile personal station within a preset range; and when another mobile personal station is detected, establishing a connection to the another mobile personal station, and sending data to the second personal station, so that the another mobile personal station manages the body device according to the data when the mobile personal station runs out of power.

Optionally, after the setting the body device according to the body parameter, the location parameter, and the communication mode supported by the body device, the following is further included:

determining, according to the body parameter, a unique recognizable characteristic of the user that carries the mobile personal station;

establishing a security authentication manner with a gateway according to the unique recognizable characteristic of the user;

collecting a physiological characteristic of the user within a preset time by using the body device, and obtaining a collection result; and interacting with the gateway according to the collection result and the security authentication manner, for identity authentication on the user.

Optionally, after the setting the body device according to the body parameter, the location parameter, and the communication mode supported by the body device, the following is further included:

detecting strength of a radio signal of the body device;

determining a distance between the body device and the mobile personal station according to the strength of the radio signal of the body device; and when the distance is greater than a preset value, sending, in a preset manner, an alert to the user that carries the mobile personal station.

Optionally, before the obtaining an identifier of a body device, the following is further included:

receiving a connection request sent by the body device, where the connection request includes the identifier of the body device;

detecting whether the identifier of the body device has already been stored; and establishing a connection to the body device when the identifier of the body device has already been stored; and the obtaining an identifier of a body device specifically includes:

obtaining the identifier of the body device that has been connected.

Optionally, the connection request further includes a parameter of the body device.

After the detecting whether the identifier of the body device has already been stored, the following is further included:

when the identifier of the body device has not yet been stored, checking, by the mobile personal station, whether the identifier of the body device is valid; and when the identifier of the body device is valid, establishing a connection to the body device, storing the identifier of the body device, and updating the body device list according to the parameter of the body device.

It can be learned from the foregoing that, according to the method and the apparatus for managing a body device provided in the embodiments of the present invention, a mobile personal station obtains an identifier of a body device; the mobile personal station obtains, according to the identifier of the body device, a communication mode supported by the body device; the mobile personal station obtains a body parameter and a location parameter that are of a user that carries the body device; and the mobile personal station sets the body device according to the body parameter, the location parameter, and the communication mode supported by the body device. In this way, the body device can be set quickly, which facilitates management of the body device and improves user experience.

It should be noted that, to make the description brief, the foregoing method embodiments are expressed as a series of actions. However, a person skilled in the art should appreciate that the present invention is not limited to the described action sequence, because according to the present invention, some steps may be performed in other sequences or performed simultaneously. In addition, a person skilled in the art should also appreciate that all the embodiments described in the specification are exemplary embodiments, and the related actions and modules are not necessarily mandatory to the present invention.

Content such as information exchange and an execution process between the modules in the apparatus and the system is based on a same idea as the method embodiments of the present invention. Therefore, for detailed content, refer to descriptions in the method embodiments of the present invention, and details are not described herein again.

A person of ordinary skill in the art may understand that all or some of the processes of the methods in the embodiments may be implemented by a computer program instructing relevant hardware. The program may be stored in a computer readable storage medium. When the program runs, the processes of the methods in the embodiments are performed. The foregoing storage medium may be a magnetic disk, an optical disc, a read-only memory (Read-Only Memory, ROM), a RAM, or the like.

Specific examples are used in this specification to describe the principle and implementation manners of the present invention. The descriptions of the foregoing embodiments are merely intended to help understand the method and idea of the present invention. In addition, with respect to the implementation manners and the application scope, modifications may be made by a person of ordinary skill in the art according to the idea of the present invention. Therefore, this specification shall not be construed as a limitation on the present invention.

What is claimed is:

1. A method for managing a body device, wherein the method comprises:

obtaining, by a mobile personal station, an identifier of a body device;

obtaining, by the mobile personal station according to the identifier of the body device, a communication mode supported by the body device;

obtaining, by the mobile personal station, a body parameter and a location parameter that are of a user that carries the body device; and setting, by the mobile personal station, the body device according to the body parameter, the location parameter, and the communication mode supported by the body device;

after the setting, by the mobile personal station, the body device according to the body parameter, the location parameter, and the communication mode supported by the body device, further comprising:

detecting, by the mobile personal station, whether there is another mobile personal station within a preset range; and establishing a connection to the another mobile personal station, and sending data received by the mobile personal station to the another mobile personal station when another mobile personal station is detected, so that the another mobile personal station manages, when the mobile personal station runs out of power, the body device according to the data sent by the mobile personal station.

2. The method according to claim 1, before the setting, by the mobile personal station, the body device according to the body parameter, the location parameter, and the communication mode supported by the body device, further comprising:

determining, by the mobile personal station, a communication priority of the body device according to the communication mode supported by the body device;

obtaining, by the mobile personal station, an ambient parameter of the user that carries the body device; and the setting, by the mobile personal station, the body device according to the body parameter, the location parameter, and the communication mode supported by the body device comprises:

setting, by the mobile personal station, the body device according to the body parameter, the location parameter, the ambient parameter, and the communication priority.

3. The method according to claim 1, after the setting, by the mobile personal station, the body device according to the body parameter, the location parameter, and the communication mode supported by the body device, further comprising:

obtaining, by the mobile personal station, data sent by the body device;

identifying, by the mobile personal station, an event type of the data;

performing, by the mobile personal station, matching between the event type of the data and a preset event; and processing, by the mobile personal station, the data and sending an alert in a preset manner according to a processing result when the event type of the data successfully matches a preset event.

4. The method according to claim 3, wherein the method further comprises:

obtaining, by the mobile personal station, a data reporting solution, wherein the data reporting solution is used to indicate whether to report after-preprocessing data or report before-preprocessing data to an information center when the event type of the data does not match a preset event; and sending, by the mobile personal station, the before-preprocessing data to the information center when the data reporting solution indicates reporting the before-preprocessing data to the information center, so that the information center processes the reported before-preprocessing data; or when the data reporting solution indicates reporting the after-preprocessing data to the information center, preprocessing, by the mobile personal station, the data and sending the after-preprocessing data to the information center, so that the information center processes the reported after-preprocessing data further.

5. The method according to claim 4, after the obtaining a data reporting solution, further comprising:

obtaining, by the mobile personal station, a network status of a network on which the mobile personal station is located; and the sending, by the mobile personal station, the before-preprocessing data to the information center when the data reporting solution indicates reporting the before-preprocessing data to the information center, so that the information center processes the reported before-processing data comprises:

sending, by the mobile personal station, the before-preprocessing data to the information center when the data reporting solution indicates reporting the before-preprocessing data to the information center and when the status of the network meets a preset network status requirement, so that the information center processes the data.

6. The method according to claim 1, after the setting, by the mobile personal station, the body device according to the body parameter, the location parameter, and the communication mode supported by the body device, further comprising:

obtaining, by the mobile personal station, a network topology of the network on which the mobile personal station is located; and optimizing the network on which the mobile personal station is located, according to communication modes supported by body devices on the network on which the mobile personal station is located, a preset optimization algorithm, and the network topology.

7. The method according to claim 1, after the setting, by the mobile personal station, the body device according to the body parameter, the location parameter, and the communication mode supported by the body device, further comprising:

determining, by the mobile personal station according to the body parameter, a unique recognizable characteristic of the user that carries the mobile personal station;

establishing, by the mobile personal station, a security authentication manner with a gateway according to the unique recognizable characteristic of the user;

collecting, by the mobile personal station, a physiological characteristic of the user within a preset time by using the body device, and obtaining a collection result; and interacting, by the mobile personal station, with the gateway according to the collection result and the security authentication manner, for identity authentication on the user.

8. The method according to claim 1, after the setting, by the mobile personal station, the body device according to the body parameter, the location parameter, and the communication mode supported by the body device, further comprising:

detecting, by the mobile personal station, strength of a radio signal of the body device;

determining, by the mobile personal station, a distance between the body device and the mobile personal station according to the strength of the radio signal of the body device; and sending, by the mobile personal station, in a preset manner, an alert to the user that carries the mobile personal station when the distance is greater than a preset value.

9. The method according to claim 1, before the obtaining, by a mobile personal station, an identifier of a body device, further comprising:

receiving, by the mobile personal station, a connection request sent by the body device, wherein the connection request comprises the identifier of the body device;

detecting, by the mobile personal station, whether the identifier of the body device has already been stored; and establishing, by the mobile personal station, a connection to the body device when the identifier of the body device has already been stored; and the obtaining, by a mobile personal station, an identifier of a body device specifically comprises:

obtaining, by the mobile personal station, the identifier of the body device that has been connected.

10. The method according to claim 9, wherein the connection request further comprises a parameter of the body device; and after the detecting, by the mobile personal station, whether the identifier of the body device has already been stored, further comprising:

checking, by the mobile personal station, whether the identifier of the body device is valid when the identifier of the body device has not yet been stored; and establishing, by the mobile personal station, a connection to the body device, storing the identifier of the body device, and updating a body device list according to the parameter of the body device when the identifier of the body device is valid.

11. An apparatus for managing a body device, wherein the apparatus is a mobile personal station and comprises:

a memory; and a processor coupled to the memory, wherein the processor is operable to:

obtain an identifier of a body device; obtain, according to the identifier of the body device, a communication mode supported by the body device; and obtain a body parameter and a location parameter that are of a user that carries the body device; and set the body device according to the body parameter, the location parameter, and the communication mode supported by the body device;

detect whether there is another mobile personal station within a preset range; and establish a connection to the another mobile personal station, and send data received by the mobile personal station to another mobile second personal station when another mobile personal station is detected, so that the another mobile personal station manages, when the mobile personal station runs out of power, the body device according to the data sent by the mobile personal station.

12. The apparatus according to claim 11, wherein the processor is further operable to:

determine a communication priority of the body device according to the communication mode supported by the body device;

obtain an ambient parameter of the user that carries the body device; and set the body device according to the body parameter, the location parameter, and the ambient parameter and according to the communication priority.

13. The apparatus according to claim 11, wherein the processor is further operable to:

obtain data sent by the body device;

identify an event type of the data;

perform matching between the event type of the data and a preset event; and process the data and send an alert in a preset manner according to a processing result when the event type of the data successfully matches a preset event.

14. The apparatus according to claim 13, wherein the processor is further operable to:

obtain a data reporting solution when the event type of the data does not match a preset event, wherein the data reporting solution is used to indicate whether to report after-preprocessing data or report before-preprocessing data to an information center;

send the before-preprocessing data to the information center when the data reporting solution indicates reporting the before-preprocessing data to the information center, so that the information center processes the reported before-preprocessing data; and preprocess the data and send the after-preprocessing data to the information center when the data reporting solution indicates reporting the after-preprocessing data to the information center, so that the information center processes the reported after-preprocessing data further.

15. The apparatus according to claim 14, wherein the processor is further operable to:

obtain a network status of a network on which the mobile personal station is located; and send the before-preprocessing data to the information center when the data reporting solution indicates reporting the before-preprocessing data to the information center and when the status of the network meets a preset network status requirement, so that the information center processes the data.

16. The apparatus according to claim 11, wherein the processor is further operable to:

obtain a network topology of the network on which the mobile personal station is located; and optimize the network on which the mobile personal station is located, according to communication modes supported by body devices on the network on which the mobile personal station is located, a preset optimization algorithm, and the network topology.

17. The apparatus according to claim 11, wherein the processor is further operable to:

determine, according to the body parameter a unique recognizable characteristic of the user that carries the mobile personal station;

establish a security authentication manner with a gateway according to the unique recognizable characteristic of the user;

collect a physiological characteristic of the user within a preset time by using the body device, and obtain a collection result; and interact with the gateway according to the collection result obtained by the collection unit and according to the security authentication manner established by the negotiation unit, for identity authentication on the user.

18. The apparatus according to claim 11, wherein the processor is further operable to:

detect strength of a radio signal of the body device set by the setting unit;

determine a distance between the body device and the mobile personal station according to the strength of the radio signal of the body device; and send, in a preset manner, an alert to the user that carries the mobile personal station when the distance is greater than a preset value.

19. The apparatus according to claim 11, wherein the processor is further operable to:

receive a connection request sent by the body device, wherein the connection request comprises the identifier of the body device;

detect whether the identifier of the body device has already been stored;

establish a connection to the body device when the identifier of the body device has already been stored; and obtain the identifier of the body device that has been connected by the connection unit.

20. The apparatus according to claim 19, wherein the processor is further operable to:

check whether the identifier of the body device is valid when the identifier of the body device has not yet been stored; and establish a connection to the body device, store the identifier of the body device, and update the body device list according to the parameter of the body device when the identifier of the body device is valid.

* * * * *